US010646529B2

(12) United States Patent
Raskin et al.

(10) Patent No.: US 10,646,529 B2
(45) Date of Patent: May 12, 2020

(54) METHODS OF OBTAINING NATURAL PRODUCTS FROM THE COMESTIBLE FLUIDS AND METHODS OF USE

(75) Inventors: Ilya Raskin, Manalapan, NJ (US); Diana Roopchand, Highland Park, NJ (US); Slavko Komarnytsky, Somerset, NJ (US)

(73) Assignee: BOARD OF TRUSTEES, RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 904 days.

(21) Appl. No.: 13/583,172

(22) PCT Filed: Mar. 14, 2011

(86) PCT No.: PCT/US2011/028347
§ 371 (c)(1),
(2), (4) Date: Nov. 19, 2012

(87) PCT Pub. No.: WO2011/115910
PCT Pub. Date: Sep. 22, 2011

(65) Prior Publication Data
US 2013/0066048 A1 Mar. 14, 2013

Related U.S. Application Data

(60) Provisional application No. 61/381,410, filed on Sep. 9, 2010, provisional application No. 61/314,017, filed on Mar. 15, 2010.

(51) Int. Cl.
*A61K 36/48* (2006.01)
*A23L 33/125* (2016.01)
*A23L 5/00* (2016.01)
*A23L 7/00* (2016.01)
*A23L 2/04* (2006.01)
*B01D 15/02* (2006.01)
*A23L 11/00* (2016.01)
*A23L 33/19* (2016.01)
*A23L 33/185* (2016.01)
*A23L 5/20* (2016.01)
*A23L 7/10* (2016.01)
*A23L 29/30* (2016.01)
*A23L 33/105* (2016.01)
*A23L 31/10* (2016.01)

(52) U.S. Cl.
CPC ............... *A61K 36/48* (2013.01); *A23L 2/04* (2013.01); *A23L 5/00* (2016.08); *A23L 5/27* (2016.08); *A23L 7/00* (2016.08); *A23L 7/115* (2016.08); *A23L 7/198* (2016.08); *A23L 11/07* (2016.08); *A23L 29/30* (2016.08); *A23L 33/105* (2016.08); *A23L 33/125* (2016.08); *A23L 33/185* (2016.08); *A23L 33/19* (2016.08); *B01D 15/02* (2013.01); *A23L 31/10* (2016.08); *A61K 2236/00* (2013.01)

(58) Field of Classification Search
None
See application file for complete search history.

(56) References Cited

U.S. PATENT DOCUMENTS

| 4,061,792 | A | * | 12/1977 | Inagami | ............... | A23C 9/1307 |
| | | | | | | 426/330.2 |
| 4,160,042 | A | * | 7/1979 | Farr | ........................ | A23F 3/385 |
| | | | | | | 426/387 |
| 6,544,581 | B1 | | 4/2003 | Shrikhande et al. | | |
| 2002/0136783 | A1 | | 9/2002 | Singh et al. | | |
| 2002/0168429 | A1 | | 11/2002 | Mann | | |
| 2002/0197303 | A1 | | 12/2002 | Kim | | |
| 2004/0161524 | A1 | | 8/2004 | Sakai et al. | | |
| 2006/0134286 | A1 | | 6/2006 | Maeda | | |
| 2007/0202195 | A1 | | 8/2007 | Wang et al. | | |
| 2007/0286938 | A1 | | 12/2007 | Saiki et al. | | |
| 2010/0015306 | A1 | | 1/2010 | Pereyra | | |
| 2010/0021615 | A1 | | 1/2010 | Sato et al. | | |
| 2010/0055248 | A1 | | 3/2010 | Woelfel et al. | | |

FOREIGN PATENT DOCUMENTS

| JP | 77031039 | B | * | 9/1977 |
| JP | 05086394 | A | * | 4/1993 |
| JP | 11346649 | A | * | 12/1999 |
| JP | 2002068991 | A | * | 3/2002 |

(Continued)

OTHER PUBLICATIONS

Denneson, L. "Daring to Thrive: Gluten-free cooking, wellness, nutrition, and living a positively thriving, engaged life". Web publication date: Oct. 7, 2008 [Retrieved from the Internet on: Sep. 21, 2016]. Retrieved from the Internet: <URL: http://daringtothrive.blogspot.com/2008/10/success-is-crispy-healthy-gluten-free.html>.*
Hoffman et al. Journal of Sports Science and Medicine (2004) 3, 118-130 (Year: 2004).*
Ekanayake et al. United States Statutory Invention Registration. H1628. Jan. 7, 1997 (Year: 1997).*
Raskin et al., Can an apple a day keep the doctor away? *Curr. Pharm. Design*, 10:3419-29 (2004).
Schmidt et al., A natural history of botanical therapeutics, *Metabolism*, 57:S3-9 (2008).
Schmidt et al., Revisiting the ancient concept of botanical therapeutics, *Nat. Chem. Biol.*, 3:360-6 (2007).

(Continued)

*Primary Examiner* — Amy L Clark
(74) *Attorney, Agent, or Firm* — Marshall, Gerstein & Borun LLP

(57) ABSTRACT

Described herein is an enriched substance containing a ground edible material comprising one or more concentrated bioactive natural products from plant juice, as well as methods of producing such enriched substances and methods of using such solids to provide beneficial effects to humans or other animals. Enriched foods comprising the enriched substance(s) are also provided. Also provided are non-sorbed natural products such as sugars, fats oils, and carotenoids found in the non-sorbed plant liquor fraction of plant juice.

9 Claims, No Drawings

(56) References Cited

FOREIGN PATENT DOCUMENTS

| JP | 2009225702 A | * | 10/2009 | ........... A23K 20/111 |
| KR | 20040098612 A | * | 11/2004 | |
| SU | 1735349 A1 | * | 5/1992 | |

OTHER PUBLICATIONS

Sun et al., Critical factors of vanillin assay for catechins and proanthocyanidins, *J. Agric. Food Chem.*, 46:4267-74 (1998).

Tomarelli et al., The use of azoalbumin as a substrate in the colorimetric determination or peptic and tryptic activity, *J. Lab. Clin. Med.*, 34(3):428-33 (1949).

Wang et al., an LC-MS method for analyzing total resveratrol in grape juice, cranberry juice, and in wine, *J. Agric. Food Chem.*, 50:431-5 (2002).

International Preliminary Report on Patentability, PCT/US2011/028347, dated Sep. 18, 2012.

International Search Report and Written Opinion of the International Searching Authority, United States Patent Office, PCT/US2011/28347, dated May 3, 2011.

Extended European Search Report, EP Application No. 11756803.0, dated Dec. 22, 2014.

Grace et al., Hypoglycemic activity of a novel anthocyanin-rich formulation from lowbush blueberry, Vaccinium angustifolium Aiton, *Phytomedicine*, 16(5):406-415 (2009).

Prepn. of ginseng tea having coffee taste by three step roasting of by-prod. ginseng or ginseng extract, bean and barley, pulverizing, extracting and specifically concentrating, *WPI Derwent* (1993). Abstract only.

* cited by examiner

METHODS OF OBTAINING NATURAL PRODUCTS FROM THE COMESTIBLE FLUIDS AND METHODS OF USE

BACKGROUND

It is well known that many foods contain numerous health/wellness-promoting and disease-preventing/curing compounds (Schmidt et al., Nat. Chem. Biol., 3:360-366, 2007; Raskin et al., Curr. Pharm. Design, 10:3419-3429, 2004). Plants are a particularly rich source of such compounds. Unfortunately, the co-evolution of people and edible plants and the advance of modern agriculture have favored the reduction of beneficial, bioactive natural products in plant foods (Schmidt et al., Met. Clin. Exp., 57:S3-S9, 2008). Extensive plant breeding and selection has reduced the content of healthy ingredients, such as various antioxidants, polyphenols, bioflavonoids, glucosinolates, healthy fibers, fatty acids, vitamins, and minerals in most plant foods (Schmidt et al., supra). This reduction was caused by the need to maximize the caloric content, palatability, and digestibility of plant foods by directing plant metabolism to accumulating starches, sugars, oils, and/or major proteins in edible parts at the expense of losing bioactive secondary metabolites. As a result, many health promoting- and disease-fighting natural products and bioactives were reduced to levels where average daily consumption cannot produce measurable health benefits. To supply a beneficial amount of plant-derived bioactives, food plants are then extracted with solvents and sold in oral form as concentrated supplements.

Ion-exchange chromatography can be used for concentrating and isolating a great variety of compounds. It is based on specific electrostatic interactions between charges on the surface of solubilized compounds and solid ion exchangers (resins). As a result, some compounds bind to the ion exchange matrix, while others remain in the solution. Ion-exchangers and compounds should be in the same polarity range to effectively bind to each other. However, ion-exchange chromatography is very expensive because it uses synthetic resins and organic solvents to elute bound phytochemicals from resins. In addition to high cost, this method is often not allowed in food manufacturing and cannot be called "natural" or "organic."

SUMMARY OF THE INVENTION

The present disclosure is based on the discovery that ingestible sorbing material effectively binds and retains sorbable natural products obtainable from plant material (e.g., by homogenization, extraction, squeezing or juicing) as well as from dairy products. As described herein, the ingestible sorbing material generally does not sorb high-calorie sugars or fats associated with most commercial fruit juices. This discovery enables a one-step concentration and separation of sorbable natural products (e.g., phytochemicals of moderate hydrophilicity and/or hydrophobicity from plant juice or protein from dairy products or from plant juice containing protein) from the non-sorbable sugars, fats, oils and other components of conventional plant extracts (or milk products). These methods also provide for the immobilization of these sorbable natural products on the healthy, nutritious, and low-sugar food matrix provided by the ingestible sorbing material, e.g., when in the form of a ground edible plant material.

Disclosed herein, in one aspect, is a method of obtaining natural products from a comestible fluid comprising (a) combining the comestible fluid with an ingestible sorbing material to form
 (i) an admixture containing an enriched substance comprising a natural product from the comestible fluid sorbed to the ingestible sorbing material; and
 (ii) a liquor comprising a non-sorbed natural product from the comestible fluid; and
(b) separating the enriched substance and the liquor, thereby obtaining the sorbed natural product and the non-sorbed natural product from the comestible fluid.

The comestible fluid is, in some embodiments, plant juice, a dairy product, or a plant juice containing protein as these terms are defined herein.

In another aspect, described herein is a method of concentrating a sorbable natural product from plant juice in edible form comprising: combining the plant juice with a ground edible material to form an admixture containing an enriched substance comprising a sorbed natural product from the plant juice; and a plant liquor comprising a non-sorbed natural product from the plant juice; and separating the enriched substance from the plant juice, thereby concentrating the sorbabl, e.g., sorbed, e natural product from the plant juice in edible form. In some embodiments, the sorbable natural products are sorbed (i.e., absorbed and/or adsorbed), to the ground edible material. In one embodiment, the sorbable natural products are adsorbed to the ground edible material. In some embodiments, the enriched substance is subsequently incorporated into a consumer product. For example, in one embodiment, the enriched substance is incorporated into a food product. In other embodiments, the enriched substance is incorporated into a cosmetic product or a pharmaceutical product.

Also provided, in another aspect, is a method of producing a plant liquor from plant juice comprising combining plant juice with a ground edible material to form an admixture containing an enriched substance comprising a sorbable natural product from the plant juice; and a plant liquor comprising a non-sorbed natural product from the plant juice; thereby producing a plant liquor from the plant juice. In some embodiments, the plant liquor is subsequently used as a food additive (e.g., natural sweetener, flavoring or coloring). In some embodiments, the soluble carbohydrates in the plant liquor are subsequently used as a natural sweetener. In other embodiments, the plant liquor is subsequently incorporated into a cosmetic product or a pharmaceutical product.

In some embodiments, if either the enriched substance or the plant liquor is incorporated into a food product, the other is not incorporated into the same food product. In other embodiments, the enriched substance and the plant liquor are incorporated into the same food product.

For any of the methods described herein, exemplary sorbable natural products include, but are not limited to, proteins, stiviol glucosides, proanthocyanidins, flavan-3-ols (catechins and catechin gallates), hydrolyzable tannins (gallotannins and ellagitannins), phlorotannins, gingerols, sesquiterpene lactones, sulforaphane, isothiocyanates, anthocyanins, resveratrol, quercetin and caffeine. In some embodiments, the sorbable natural product is a phenolic compound such as a polyphenol selected from the group consisting of an anthocyanins, a proanthocyanidin, resveratrol, quercetin and a catechin.

For any of the methods described herein, exemplary non-sorbable natural products include, but are not limited to, carbohydrates (e.g., fructose or glucose), fats and oils.

Also provided in yet another aspect is a method of making an enriched food product comprising a sorbable natural product from plant juice comprising incorporating the enriched substance produced by the methods described herein into an enriched food product. In one embodiment, the enriched food product is a baked good (including, but not limited to, breads, cookies, muffins, crackers, scones, cereals and bars). In another embodiment, the enriched food product is a beverage (e.g., a smoothie, a water or dairy beverage, or a soy-based beverage).

In another embodiment, it may be desirable for the concentrated sorbed natural products to be free of the enriched substance matrix. For example, it may be desirable to incorporate the sorbed natural products alone (as opposed to being part of the enriched substance matrix), e.g., in beverage applications where the enriched substance may not dissolve completely in the beverage. This would allow the animal ingesting the beverage to have the benefits of the sorbed natural products, without the need to consume any residual enriched substance that remains once the liquid has been ingested. Thus, another aspect of the disclosure is a method as described herein that further comprises the step of separating the sorbed natural products from the enriched substance. The separation of the sorbed natural products from the enriched substance is performed using methods well known in the art and described herein, e.g., various chromatographic elution methodologies.

In some embodiments, when the ingestible sorbing material is in the form of ground edible material, the ground edible material is added to the plant juice at a concentration of at least about 5 g/L. In yet another embodiment, ground edible material is added to the plant juice at a concentration of about 5 g/L, about 10 g/L, about 20 g/L, about 30 g/L, about 40 g/L, about 50 g/L, about 60 g/L, about 70 g/L, about 80 g/L, about 90 g/L, about 100 g/L, about 110 g/L, about 120 g/L, about 130 g/L, about 140 g/L, about 150 g/L, about 160 g/L, about 170 g/L, about 180 g/L about 190 g/L or about 200 g/L.

Plant juice comprises material that has been homogenized, extracted, pressed, squeezed or juiced from a plant or plant part. Alternatively, the plant juice comprises tea, infusions, suspensions, emulsions or tinctures from a plant or plant part. The term "plant" as used herein includes both higher, or vascular, plants (e.g., fruits, vegetables, medicinal plants) and lower, or non-vascular, plants (e.g., algae and fungi). Exemplary plant parts (with respect to vascular plants) include, but are not limited to, bark, a flower (or petal thereof), a tuber, a stem, a root, a fruit, a berry, a seed, a nut and a leaf of a plant.

In some embodiments, the ingestible sorbing material is a ground edible material such as a plant flour. In one embodiment, the flour comprises at least 25 weight percent protein. In some embodiments, the flour is selected from the group consisting of soybean flour, wheat flour, almond flour, amaranth flour, brown rice flour, buckwheat flour, cassava flour, chestnut flour, chickpea flour, chuno flour, corn flour, cornstarch, glutinous rice flour, noodle flour, hazelnut flour, walnut flour, pea flour, peanut flour, potato starch flour, rice flour, rye flour, tapioca flour, teff flour, arrowroot flour, taro flour, quinoa flour, mulga flour, ironweed flour, umbrella bush flour, tjuntjula flour, wakalpulka flour, witchetty bush flour, wiry wattle flour, Mitchell grass flour, nardoo flour, coconut flour, old man saltbush flour and wangunu flour.

In some embodiments, the flour is soybean flour, for example, defatted soybean flour. The use of other ground edible materials such as protein powder, including, but not limited to, soy protein concentrate, soy protein isolate, wheat bran, oat bran, barley bran, rice bran, milk powder, egg powder, whey protein, gluten and yeast powder, and cellulose- or chitin-containing material including, but not limited to, non-soluble vegetable fibers is also contemplated.

The enriched substance produced by a method described herein can be separated from the plant liquor by any means known in the art. In one embodiment, the enriched substance is separated from the plant liquor by a method selected from the group consisting of centrifugation, filtration and sedimentation.

In some embodiments, the enriched substance comprises at least about 3 mg/g of the concentrated sorbable natural product(s).

In any of the ranges described herein, the endpoints of the range are included in the range. Additional features and variations of the invention will be apparent to those skilled in the art from the entirety of this application and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION

Definitions:

The term "comestible fluid" as used herein refers to any fluid that may be ingested by at least one mammal without producing adverse effects when consumed by the mammal. Exemplary comestible fluids include "plant juice," "plant juice containing protein" or "juice of a unicellular organism" as these terms are described herein as well as dairy products including, but not limited to, milk, yogurt and kefir.

The term "plant juice" as used herein refers to plant material that has been homogenized, extracted, squeezed or juiced from a plant or plant part. "Plant juice" also refers to plant material that is made into teas, infusions, tinctures, suspensions, emulsions and combinations thereof that are made from plant material. In one embodiment, the plant juice may be prepared by drawing out, withdrawing, distilling or otherwise separating one substance from another by a chemical or physical process. The plant material will typically be fragmented by slicing, pulverizing, grinding or by any other technique known in the art to increase surface area and thereby facilitate exposure to a fluid such as a solvent (e.g., water or alcohol) in preparation of a plant juice.

The term "plant juice containing protein" as used herein simply refers to any plant juice (as defined herein) comprising protein. Plant juice comprising protein can be produced from plants (or plant parts) comprising some amount of protein including, but not limited to, a potato, papaya, soybean, asparagus, broccoli, a peanut, cauliflower, a pea, soybean, a green bean, a walnut, cantaloupe, celery, avocado, strawberry, rice, an orange and a pineapple.

The term "ingestible sorbing material" as used herein refers to any material (liquid or solid) capable of sorbing natural products as that term is defined herein. The term "ingestible sorbing material" encompasses "ground edible material" as that term is described herein as well as phenolic compounds (e.g., anthocyanins, proanthocyanidins or hydrolyzable tannins), which may be present, for example, in plant juices. It will be apparent that this term is used in a context-specific manner in that a given compound or substance may be an ingestible sorbing material depending on whether it sorbs at least one compound or substance to which it is exposed. In some embodiments, the ingestible sorbing material itself can also provide health benefits to a mammal when ingested and in some cases provide the majority of health benefits (compared to the substance sorbing to the ingestible sorbing material).

The term "ground edible material" as used herein refers to any edible solid material that has been processed to increase its surface area, such as by grinding or milling by methods known in the art. In some embodiments, the ground edible material is derived from a plant or microbe that has been processed to increase its surface area, such as by shearing, grinding or milling, using any method known in the art. Grinding, milling, or pulverizing plant material is preferred because it greatly increases the surface area of the edible material. In some embodiments, the ground edible material is a plant flour. The use of other ground edible materials such as soybean protein concentrate, soybean protein isolate, protein powder (including, but not limited to, milk powder, egg powder, whey protein, gluten and yeast powder) and cellulose- or chitin-containing material (including, but not limited to, non-soluble vegetable fibers) is also contemplated. In other embodiments, the ground edible material is a bran, produced from the outer layer of plant seeds. Bran includes, but is not limited to, wheat bran, corn bran, rice bran, oat bran and barley bran.

The term "enriched substance" as used herein refers to ingestible sorbing material (e.g., ground edible material or phenolic compounds) containing one or more sorbable natural products sorbed from a comestible fluid (e.g., plant juice or fluid or juice obtained from a unicellular organism).

The term "sorbable natural product" or "sorbed natural product" as used herein means a compound present in plant juice (or dairy product) that becomes associated (e.g., by absorption or adsorption) with an ingestible sorbing material and that is intended to improve the general health or wellness of an animal such as a mammal and that provides a nutritional or therapeutic benefit to the animal when consumed. Exemplary sorbable natural products include, but are not limited to, proteins, stiviol glucosides, and phytochemicals such as polyphenols, anthocyanins/proanthocyanidins, bioflavenoids, carotenoids, catechins, glucosinolates, organosulphides, gingerols and phytoestrogens. As for ingestible sorbing material, a sorbable natural product is a term used in a context-specific manner in that a given compound or substance is a sorbable natural product if it sorbs to an ingestible sorbing material to which it has been exposed.

The term "non-sorbable natural product" or "non-sorbed natural product" as used herein means a compound present in plant juice (or dairy product) that is intended to taste good, improve the palatability of food with which it is associated, color a food product, or color non-food substances (e.g., textiles, plastics, paints and finishes), but may not provide a therapeutic benefit to a mammal when consumed other than providing an energy source. In rare circumstances it would be apparent to one of skill from the disorder, disease or condition of an animal ingesting a non-sorbed natural product, that a non-sorbed natural product may be therapeutic in providing, e.g., a fat or oil to treat a lipid disorder, disease or condition or sugars to treat a hypoglycemic disorder, disease or condition. The non-sorbable natural product comprises, in some embodiments, any compound present in the plant juice (or dairy product) that is not a sorbable natural product as defined herein. In some embodiments, the non-sorbable natural product is selected from the group consisting of soluble carbohydrates, fats and oils. In some embodiments, the non-sorbable natural product is a soluble carbohydrate. In some embodiments, the soluble carbohydrate is a sugar selected from the group consisting of fructose, glucose, sucrose, galactose, raffinose, stachyose, maltose and lactose.

The term "natural product(s)" as used herein encompasses both sorbable and non-sorbable natural products.

The term "liquor" as used herein refers to the liquid remaining after the comestible fluid has been in contact with the ingestible sorbing material. The liquor retains the non-sorbable natural products from the comestible fluid in whereas the ingestible sorbing material retains the sorbable natural products from the comestible fluid. For example, when the comestible fluid is plant juice, the liquor (or plant liquor) retains the non-sorbable natural products from the plant juice whereas the ingestible sorbing material (e.g., ground edible material) retains the sorbable natural products from the plant juice.

The term "plant" as used herein includes both higher, or vascular, plants (e.g., fruits, vegetables, medicinal plants) and lower, or non-vascular, plants (e.g., algae and fungi), as well as unicellular yeast. Exemplary plant parts (with respect to vascular plants) include, but are not limited to, bark, a flower (or petal thereof), a tuber, a stem, a root, a fruit, a berry, a seed, a nut and a leaf of a plant.

The term "extract" may be a single extract obtained from a particular extraction step or series of extraction steps or the extract may be a combination of extracts obtained from separate extraction steps. Such combined extracts are thus also encompassed by the term "extract." Solvents for use in extraction methods include water and well-known organic solvents such as, but not limited to, alcohols, alkanes, halocarbons, ethers, aromatic solvents, ketones, aqueous solvents, esters, and supercritical fluids. In one embodiment, ethanol is used to practice a method according to the disclosure. Like water, a benefit of incorporating an ethanolic solvent in the final extraction step is that an ethanolic solvent is compatible with an ingestible product, and therefore is suitable for incorporation into a pill, capsule, tablet, and other ingestible forms known in the art.

As used herein, the term "sorb" refers to adsorb, absorb, or a combination thereof. Analogously, the term "sorption" refers to adsorption, absorption, or a combination thereof. "Sorption" is given the meaning it has acquired in the art, i.e., the taking up and holding of one substance by another, which includes the processes of adsorption and/or absorption. The term "adsorption," is given its ordinary meaning in referring to the physical adherence or association of one substance (e.g., a sorbable natural product) to the surface of another substance (e.g., a ground edible material). Also given its ordinary meaning in the art, "absorption" refers to the taking up or incorporation of one substance (e.g., a sorbable natural product) into another substance (e.g., a ground edible material or phenolic compound(s)). The term "desorption" refers to the converse process in which a sorbed substance (e.g., a sorbable natural product) is released from an ingestible sorbing material (e.g., a ground edible material or phenolic compound(s)).

The term "admixture" as used herein refers to a composition produced by mixing or conmingling a comestible fluid with an ingestible sorbing material.

I. Methods of Obtaining Natural Products from a Comestible Fluid

The present disclosure is based on the discovery that ingestible sorbing material effectively binds and retains sorbable natural products obtainable from plant material (e.g., by homogenization, extraction, squeezing or juicing) as well as from dairy products. The sorbable natural products obtainable from plant material may be obtained as an extract, an exudate, a suspension, an emulsion, a secretion, a tea or a tincture, collectively referred to herein as a "plant juice."

As described herein, the ingestible sorbing material, when in the form of a ground edible material, generally does not sorb highly hydrophobic or highly hydrophilic natural products (e.g., calorie-rich sugars, oils or fats) associated with most commercial fruit juices. This discovery enables a one-step concentration and separation of sorbable natural products from the sugars, fats, oils, and other components of conventional plant extracts. This discovery also enables the separation of non-sorbable natural products from the sorbable natural products present in most fruit juices. In some embodiments, these methods also provide for the immobilization of the sorbable natural products within the healthy, nutritious, and low-sugar food matrix provided by ground edible plant material. The methods, described herein, also provide for the separation of non-sorbable natural products such as soluble carbohydrates (e.g., sugars), oils and fats associated with plant juice for use as natural food additives, such as sweeteners, flavorings (flavors) or colorings (colors or natural pigments).

In one aspect, disclosed herein is a method of obtaining natural products from a comestible fluid comprising (a) combining the comestible fluid with an ingestible sorbing material to form (i) an admixture containing an enriched substance comprising a natural product from the comestible fluid sorbed to the ingestible sorbing material; and (ii) a liquor comprising a non-sorbed natural product from the comestible fluid; and (b) separating the enriched substance and the liquor, thereby obtaining the sorbed natural product and the non-sorbed natural product from the comestible fluid.

The comestible fluid is, in some embodiments, plant juice, plant juice containing protein as these terms are defined elsewhere herein or a dairy product.

In another aspect, the disclosure provides a method of concentrating a sorbable natural product from plant juice in edible form comprising combining the juice with a ground edible material to form an admixture containing an enriched substance comprising the sorbed natural product from the plant juice; and separating the enriched substance from the juice, thereby concentrating the sorbable natural product in edible form from the juice. In some embodiments, the enriched substance is formulated into an edible food product.

It is desirable, in some embodiments, to produce a plant liquor comprising non-sorbable natural products present in the comestible fluid (e.g., plant juice) that do not sorb (or sorb weakly) to the ingestible sorbing material (e.g., ground edible material). For example, in another aspect, the disclosure provides a method of producing a plant liquor from plant juice comprising combining the plant juice with a ground edible material to form an admixture containing an enriched substance comprising a sorbed natural product from the plant juice and a plant liquor comprising a non-sorbed natural product from the plant juice; thereby producing a plant liquor from the plant juice.

In some embodiments, the amount of ingestible sorbing material that is in contact with the comestible fluid may be insufficient to achieve quantitative sorption of a sorbable natural product, or the flow rate of the comestible fluid over the ingestible sorbing material may be incompatible with quantitative sorption, resulting in less than 100% of the sorbable natural products (as defined herein) present in the comestible fluid being sorbed to the ingestible sorbing material. For example, once the ingestible sorbing material has reached the point of saturation, sorbable natural products, which under optimal conditions would have sorbed to the ingestible sorbing material, remain in solution in the liquor. Such sorbable natural products could be separated from the liquor using techniques well known in the art and described elsewhere herein. In one embodiment, the liquor is contacted with an ingestible sorbing material as described herein to sorb any residual sorbable products present in the liquor to the ingestible sorbing material.

In some embodiments, at least 40% of the sorbable natural products present in the comestible fluid are sorbed to the ingestible sorbing material. In other embodiments, at least 45%, at least 50%, at least 55%, at least 60%, at least 65%, at least 70%, at least 75%, at least 80%, at least 85%, at least 90%, at least 95%, at least 99% or more of the sorbable natural products present in the comestible fluid are sorbed to the ingestible sorbing material. Similarly, in some embodiments, less than 40% of the sorbable natural products are present in the liquor. In other embodiments, less than 35%, less than 30%, less than 25%, less than 20%, less than 15%, less than 10%, less than 5% or less of the sorbable natural products are present in the liquor.

In some embodiments, less than 5% of the non-sorbable products (e.g., soluble carbohydrates) present in the comestible fluid (e.g., plant juice) are sorbed to the ingestible sorbing material (e.g., ground edible material). In other embodiments, less than 20%, less than 10%, less than 5%, less than 4%, less than 3%, less than 2% or less than 1% of the non-sorbable products (e.g., soluble carbohydrates) present in the comestible fluid (e.g., plant juice) are sorbed to the ingestible sorbing material (e.g., ground edible material).

In certain exemplary embodiments, and under the conditions provided in the Examples, the ground edible material sorbed about 30%-60% of the anthocyanins present in blueberry juice; about 30%-70% of the anthocyanins, about 85% of the resveratrol and about 74% of the quercetin present in grape juice; about 30%-80% of the catechins and about 19% of caffeine present in tea; and about 40%, 100% and 80% of the dihydrolactucin, lactucopicrin and dihydrolactucopicrin compounds, respectively, present in chicory root extract.

As used herein, the term "sorb" refers to adsorb, absorb, or a combination thereof. Analogously, the term "sorption" refers to adsorption, absorption, or a combination thereof. "Sorption" is given the meaning it has acquired in the art, i.e., the taking up and holding of one substance by another, which includes the processes of adsorption and/or absorption. The term "adsorption," is given its ordinary meaning in referring to the physical adherence or association of one substance (e.g., a sorbable natural product) to the surface of another substance (e.g., a ground edible material). Also given its ordinary meaning in the art, "absorption" refers to the taking up or incorporation of one substance (e.g., a sorbable natural product) into another substance (e.g., a ground edible material or phenolic compound(s)). The term "desorption" refers to the converse process in which a sorbed substance (e.g., a sorbable natural product) is released from an ingestible sorbing material (e.g., a ground edible material or phenolic compound(s)).

With respect to adsorption, and without wishing to be bound to any particular theory, the adsorption of the sorbable natural products to the ground edible material (to produce an enriched substance) appears to based on the ion exchange properties and large surface area of the ground edible material that enable the material to bind to moderately charged sorbable natural products obtainable from plant juice, while highly charged, non-sorbable natural products such as polar carbohydrates and sugars and poorly charged, non-polar fats and oils remain in solution in the plant juice. The ground edible material has a propensity to adsorb natural products of intermediate polarity. Relatively hydrophobic (non-polar), oil-soluble compounds such as carotenoids and polar, highly water-soluble sugars are poorly adsorbed. This property allows for efficient, low-cost concentration of sorbable natural products obtained from a comestible fluid in a food matrix provided by the ground edible material described herein. This property also allows for efficient separation of non-sorbable natural products from plant juice for use as pleasant-tasting food additives (e.g., natural sweeteners), flavorings or colorings.

In another aspect, disclosed herein is a method of concentrating one or more natural products obtainable from a juice of a unicellular organism (e.g., yeast, bacterium) comprising combining the juice with an ingestible sorbing material such as a ground edible material to form an admixture containing an enriched substance; and separating the enriched substance from the juice, thereby concentrating the natural products from the juice in edible form. In one embodiment, the unicellular organism is yeast.

Another aspect of the present disclosure is a method of obtaining protein from a comestible fluid (e.g., dairy product or plant juice containing protein). For example, in some embodiments, the method comprises (a) combining the comestible fluid with an ingestible sorbing material to form (i) an admixture containing an enriched substance comprising protein from the comestible fluid sorbed to the ingestible sorbing material and (ii) a liquor comprising a non-sorbed natural product from the comestible fluid; (b) separating the enriched substance and the liquor, thereby obtaining the protein from the comestible fluid. In some embodiments, the comestible fluid is milk. In other embodiments, the comestible fluid is a plant juice containing protein obtainable from a plant or plant part selected from the group consisting of a potato, papaya, soybean, asparagus, broccoli, a peanut, cauliflower, a pea, a soybean, a green bean, a walnut, a cantaloupe, celery, an avocado, a strawberry, rice, an orange and a pineapple.

II. Sorbable Natural Products

In one embodiment, the sorbable natural product is a phenolic compound. Phenolic compounds are characterized by having at least one aromatic ring with one or more hydroxyl groups (Crozier, A., I. B. Jaganathb, M. N. Clifford. 2009. Dietary phenolics: chemistry, bioavailability and effects on health. Nat. Prod. Reports. 26: 1001-1043). Many phenolic compounds can be derivatized (e.g., esterified or glucosylated) and/or form dimers, oligomers or polymers. Basic skeletons of non-derivatized phenolics include, but are not limited to, phenolic acids, acetophenones, phenylacetic acids, hydroxycinnamic acids, coumarins, naphthoquinones, xanthones, stilbenes, and flavonoids. Flavonoids are the most numerous of the phenolics and have numerous health benefits. The main subclasses of dietary flavonoids are flavonols, flavones, flavan-3-ols, anthocyanidins, flavanones and isoflavones, dihydroflavonols, flavan-3,4-diols, coumarins, chalcones, dihydrochalcones and aurones. Polymerization of hydroxylated or esterified flavan-3-ols leads to the formation of proanthocyanidins also known as condensed or non-hydrolyzable tannins. Proanthocyanidins that consist exclusively of (epi)catechin units are called procyanidins, and are the most abundant type of proanthocyanidins in plants. The other class of tannins, hydrolyzable tannins, are derived from gallic acid.

The term "polyphenol" is often used to refer to plant phenolic compounds, which are characterized by the presence of more than one phenol unit or building block per molecule. Polyphenols are generally divided into hydrolyzable tannins and phenylpropanoids (derived from phenylalanine), such as lignin, flavonoids, and condensed tannins. Some polyphenols are not present in live plants but are formed during processing of foods and beverages, such as black tea fermentation, wine making, and coffee and cocoa production. Such polyphenols are often called "derived polyphenols."

In some embodiments, the phenolic compound is a flavonoid compound. In one embodiment, the phenolic compound is a flavonol. Flavonols are a class of flavonoids that have the 3-hydroxyflavone backbone (IUPAC name: 3-hydroxy-2-phenylchromen-4-one). Exemplary flavonols include, but are not limited to, quercetin, 3-hydroxyflavone, azaleatin, fisetin, galangin, gossypetin, kaempferide, kaempferol, isohamnetin, morin, myricetin, natsudaidain, pachypodol, rhamnazin and rhamnetin. In another embodiment, the flavonoid compound is a flavonol glycoside. Exemplary flavonol glycosides include, but are not limited to, astragalin, azalein, hyperoside, isoquercitin, kaempferitin, myricitrin, quercitrin, robinin, rutin, spiraeoside, xanthorhamnin, amuirensin, icariin and troserutin. Phenolic compounds obtainable from plant juice comprising a 3-hydroxyflavone backbone are specifically contemplated.

In another embodiment, the phenolic compound is a flavanol. Flavanols are a class of flavonoids that have the 2-phenyl-3,4-dihydro-2H-chromen-2-ol backbone. Exemplary flavanols include, but are not limited to, flavan-3-ols (e.g., catechins and catechin gallates). In some embodiments, the flavanol is a compound selected from the group consisting of fisetinidol, robinetinidol, epicatechin, mesquitol, epigallocatechin, epicatechin gallate and epigallocatechin gallate. Phenolic compounds obtainable from plant juice comprising a 2-phenyl-3,4-dihydro-2H-chromen-2-ol backbone are specifically contemplated.

In another embodiment, the phenolic compound is a flavanone. Exemplary flavanones include, but are not limited to, butin, eriodictyol, hesperetin, homoeriodictyol, isosakuranetin, naringenin, pinocembrin, sakuranetin, sakuranin, poriol, and sterubin. In one embodiment, the flavonoid compound is a glycoside of a flavanone. Exemplary flavanone glycosides include, but are not limited to, eriocitrin, hesperedin, liquiritin, naringin, narirutin, poncirin, nirurin and sakuranin.

In another embodiment, the phenolic compound is an anthocyanidin. Exemplary anthocyanidins include, but are not limited to aurantinidin, cyanidin, 6-hydroxycyanidin, delphinidin, europinidin, luteolinidin, fisetinidin, guibourtinidin, robinetinidin, pelargonidin, lamvidin, peonidin, petunidin, 5-desoxy-malvidin, capensinidin, diosmetinidin, gesneridin and rosinidin. In one embodiment, the flavonoid compound is an anthocyanin (i.e., a glycoside of an anthocyoanidin). Exemplary anthocyanins include, but are not limited to, antirrhinin (cyanidin 3-O-rutinoside), chrysanthenin (cyanidin 3-glucoside), myrtillin (delphinidin 3-O-glucoside, tulipanin (delphinidin 3-O-rutinoside)), violdelphin (delphinidin 3-rutinoside-7-O-(6-O-(4-(6-O-(4-hydroxybenzoyl)-beta-D-glucosyl)oxybenzoyl)-beta-D-glucoside), malvin (diglucoside of malvidin), oenin (malvidin 3-O-glucoside), primulin (malvidin-3-O-galactoside), pulchellidin 3-glucoside, pulchellidin 3-rhamnoside, cyanidin-3-(di-p-coumarylglucoside)-5-glucoside, commelinin (a tetranuclear (4 Mg(2+)) metal complex, in which two Mg(2+) ions chelate to six anthocyanin molecules, while the other two Mg(2+) ions bind to six flavone molecules), cyanosalvianin (a metalloanthocyanin: 3-O-(6-O-p-coumaroylglucopyranosyl)-5-O-(4-O-acetyl-6-O-malonylglucopyranosyl), delphinidin, 7,4'-di-O-glucopyranosylapigenin and magnesium ion) and protocyanin (supermolecular pigment consisting of a complex of anthocyanin, flavone, one ferric iron, one magnesium and two calcium ions).

In another embodiment, the phenolic compound is an isoflavonoid. Isoflavonoids have the 3-phenylchromen-4-one backbone. In one embodiment, the isoflavonoid is a phytoestrogen. Phenolic compounds obtainable from plant juice comprising a 3-phenylchromen-4-one backbone are specifically contemplated.

In other embodiments, the sorbable natural product is an alkaloid. In one embodiment, the alkaloid is caffeine. Caffeine is a naturally occurring xanthine alkaloid found in varying quantities in the seeds (e.g., beans), leaves, and fruit of some plants (e.g., where it acts as a natural pesticide). In humans, caffeine may have numerous beneficial effects. The most common use of caffeine as a supplement is as a central nervous system stimulant and performance enhancer, particularly in terms of mood, mental tasks and alertness (Smith et al., J Psychopharmacol. 19(6):620-6, 2005). Common sources of caffeine are coffee, tea, and, to a lesser extent, cocoa bean. Less commonly used sources of caffeine include the yerba maté and guarana plants, which are sometimes used in the preparation of teas and energy drinks. Two of caffeine's alternative names, mateine and guaranine, are derived from the names of the yerba maté and guarana plants.

One of the world's primary sources of caffeine is the coffee "bean" (which is the seed of the coffee plant), from which coffee is brewed. Caffeine content in coffee varies widely depending on the type of coffee bean and the method of preparation used; even beans within a given bush can show variations in concentration. In general, one serving of coffee ranges from 40 mg, for a single shot (30 ml) of arabica-variety espresso, to about 100 mg for a cup (120 ml) of drip coffee. In general, dark-roast coffee has less caffeine than lighter roasts because the roasting process reduces the bean's caffeine content. Arabica coffee normally contains less caffeine than the robusta variety.

Tea is another common source of caffeine. Tea is the agricultural product of the leaves, leaf buds, and internodes of *Camellia sinensis* (the "Tea plant"). Teas are prepared and cured by various methods. The aromatic beverage is typically prepared from the cured leaves by combination with hot or boiling water. There are at least six varieties of tea, i.e., white, yellow, green, oolong, black and pu-erh, of which the most commonly found on the market are white, green, oolong and black. Different tea varieties may be made from the same plant (i.e., *Camellia sinensis*), with the leaves being processed differently and, in the case of fine white tea, grown differently. Pu-erh tea, a post-fermented tea, is also often used medicinally.

The term "herbal tea" refers to an infusion or tisane of leaves, flowers, fruit, herbs or other plant material from a plant other than *Camellia sinensis*. Exemplary plants for herbal tea production are Chrysanthemum, ginger, honeysuckle, dandelion, and jasmine. The term "red tea" refers to an infusion made from either black tea or the South African rooibos plant (containing no *Camellia sinensis*).

In another embodiment, the sorbable natural product obtainable from plant juice is a terpenoid (or an isoprenoid). Terpenoids are derived from five-carbon isoprene units assembled and modified in many different ways. Classes of plant terpenoids, based on the number of isoprene units, include but are not limited to, hemiterpenoids, monoterpenoids, sesquiterpenoids, diterpenoids, sesterterpenoids, triterpenoids, tetraterpenoids and polyterpenoids. Exemplary terpenoids include artemisinin, carotenoids pigments, camphor, menthol, limonene, carvone, nepetalactone, hecogenin, digitoxigenin, chicory sesqueterpene lactones and triptolide.

In some embodiments, the sorbable natural product obtainable from plant juice is selected from the group consisting of antioxidants, carotenoids, caffeine, ecdysteroids, isothiocyanates, sesquiterpene lactones, barberine, gingerols, ginsenosides, glycycrrhizin, polymethoxylated flavones, tocotrienols, glucosinolates, punicalagins, soluble dietary fiber and organosulfur compounds from onions and garlic, as well as compounds or mixtures of compounds from Echinacea extracts, saw palmetto extracts, ginkgo extracts, black cohosh extracts, St. John's wort extracts, milk thistle extracts and vitamins (including vitamin A (retinol), vitamin $B_1$ (thiamine), vitamin C (ascorbic acid), vitamin D (calciferol), vitamin $B_2$ (riboflavin), vitamin E (tocopherol), vitamin $B_{12}$ (cyanocobalamin), vitamin K (phylloquinone), vitamin $B_5$ (pantothenic acid), vitamin $B_7$ (biotin), vitamin $B_6$ (pyridoxine), vitamin $B_3$ (niacin) and vitamin $B_9$ (folic acid)).

In one embodiment, the sorbable natural product obtainable from a comestible fluid is selected from the group consisting of proteins, stiviol glucosides, proanthocyanidins, flavan-3-ols (vatechins and catechin gallates), hydrolyzable tannins (gallotannins and ellagitannins), phlorotannins, gingerols, sesquiterpene lactones, sulforaphane, isothiocyanates, anthocyanins, resveratrol, quercetin and caffeine. Anthocyanins are present in all tissues of higher plants, including leaves, stems, roots, flowers and fruits. Plants known in the art to be rich in anthocyanins are Vaccinium species, such as acai (320 mg/100 g), blueberry (558 mg/100 g), chokeberry (1480 mg/100 g), cranberry and bilberry, Rubus berries including black raspberry (589 mg/100 g), red raspberry (365 mg/100 g), blackberry (317 mg/100 g), blackcurrant (190-270 mg/100 g), redcurrant (80-420 mg/100 g), cherry (350-400 mg/100 g), eggplant (750 mg/100 g), black rice, Concord grape (888 mg/100 g) and muscadine grape, purple corn (1642 mg/100 g), red cabbage, black soybean (2,000 mg/100 g) and violet petals. Plant juice obtainable from plants rich in anthocyanins is specifically contemplated.

Resveratrol is found in the skin of red grapes and is a constituent of red wine. Plant juice obtainable from plants rich in resveratrol is specifically contemplated.

Foods known in the art to be rich in quercetin include capers, lovage, apples, tea plant (*Camellia sinensis*), onion (especially red onion), red grapes, citrus fruit, tomato, broccoli and other leafy green vegetables, and a number of berries including cherry, raspberry, bog whortleberry, lingonberry, cranberry, chokeberry, sweet rowan, rowanberry, sea buckthorn berry, crowberry, and the fruit of the prickly pear cactus. Plant juice obtainable from plants rich in quercetin is specifically contemplated.

Catechins are polyphenolic antioxidant plant metabolites. Catechins are abundant in teas derived from the tea plant *Camelia sinensis* (including white tea, green tea, black tea and Oolong tea) as well as in some cocoas and chocolates (made from the seeds of *Theobroma cacao*). Plant juice obtainable from plants rich in catechins is specifically contemplated.

Selection of appropriate natural product(s) for combination with an ingestible sorbing material (e.g., ground edible material or phenolic compound(s)) to form an enriched substance for administration to a given animal is considered to be within the ordinary skill of a worker in the art and it is understood that natural products suitable for administration to humans may differ from those suitable for other animals. Furthermore, it will be apparent that inappropriate combinations of natural products, for example, those that counteract each other, are disfavored.

In another embodiment, the sorbable natural product from a comestible fluid are proteins. Exemplary proteins include, but are not limited to, protease inhibitors (e.g., potato protease inhibitor I and potato protease inhibitor II), proteases (e.g., papain and bromelain) and milk proteins (e.g., casein, lactoglobulin and lactalbumin).

III. Comestible Fluid

In one aspect, the comestible fluid is plant juice. Plant material used to produce the plant juice is, in some embodiments, from a fruit-producing plant selected from the group consisting of plums, apricots, peaches, apples, oranges, lemons, limes, tangerines, grapefruit, bananas, pears, cherries, grapes, tomatoes, strawberries, cranberries, blueberries, blackberries, raspberries, gooseberries, figs, pineapple, watermelon, pumpkin, cantaloupe, mango, papaya, peanuts, walnuts, pecans, almonds, cashew nuts, prunes, raisins, pineapple, cucumbers, coffee, noni and eggplant. In another embodiment, the plant material is obtainable from a vegetable plant selected from the group consisting of potatoes, onions, green onions, shallots, garlic, carrots, turnips, beets, parsnips, radishes, rutabaga, celery, mushrooms, corn, okra, spinach, cabbage, kale, lettuce, broccoli, cauliflower, string beans, soybeans, peas, cucumbers, squash, zucchini, lettuce, broccoli rabe, broccoli romanesco, rhubarb, collard greens, brussels sprout, bok choy, arugula and daikon. In yet another embodiment, the plant material is obtainable from a medicinal plant selected from the group consisting of St. John's wort, Echinacea, saw palmetto, ginkgo, ginseng, black cohosh, and milk thistle. In still another embodiment, the plant material is obtainable from a fungus including but not limited to mushrooms, such as almond mushrooms, lingzhi mushrooms, caterpillar fungus, shitake mushrooms, button mushrooms, Portobello mushrooms, straw mushrooms, oyster mushrooms, enokitake, milk mushrooms, morels, chanterelles, truffles, black trumpets and porcini mushrooms. In yet another embodiment, the plant material is obtainable from algae, such as blue green algae (e.g., Spirulina), green algae and red algae.

In rare circumstances, a plant juice as a whole may be harmful to at least one mammal and may, therefore, not be a comestible fluid as defined herein. Such potentially non-comestible fluids may contain an ingestible compound and if so, the potentially non-comestible fluid is contemplated as suitable for the methods described herein.

In another aspect, the comestible fluid is a dairy product. Exemplary dairy products include, but are not limited to, milk, yogurt and kefir.

IV. Ingestible Sorbable Material

In one aspect, the ingestible sorbing material is a ground edible material such as a plant flour. The use of other ground edible materials such as soybean protein concentrate, soybean protein isolate, protein powder (including, but not limited to, milk powder, egg powder, whey protein, gluten and yeast powder) and cellulose- or chitin-containing material (including, but not limited to, non-soluble vegetable fibers) is also contemplated. In other embodiments, the ground edible material is a bran, produced from the outer layer of plant seeds. Bran includes, but is not limited to, wheat bran, corn bran, rice bran oat bran and barley bran.

In one embodiment, the plant flour comprises at least 15 weight percent protein. In other embodiments, the flour comprises at least 20, at least 25, at least 30, at least 35, at least 40, at least 45, at least 50, at least 60, at least 65, at least 70 or more weight percent protein. In some embodiments, the plant flour is a leguminous flour. Some proteins in legume flour belong to the globulin family of seed storage proteins called leguminins (11S) and vicilins (7S), or, in the case of soybeans, glycinin and beta-conglycinin.

In specific exemplary embodiments, the plant flour is selected from the group consisting of soybean flour, wheat flour, almond flour, aramanth flour, brown rice flour, buckwheat flour, cassava flour, chestnut flour, chickpea flour, chuno flour, corn flour, cornstarch, glutinous rice flour, noodle flour, hazelnut flour, pea flour, bean flour, peanut flour, potato starch flour, rice flour, rye flour, tapioca flour, teff flour, arrowroot flour, taro flour, quinoa flour, mulga flour, ironweed flour, umbrella bush flour, tjuntjula flour, wakalpulka flour, witchetty bush flour, wiry wattle flour, Mitchell grass flour, nardoo flour, old man saltbush flour and wangunu flour.

In one embodiment, the ground edible material is selected from the group consisting of soybean flour, soybean protein concentrate and soybean protein isolate. Soybean flour contains trypsin inhibitors, hemagglutinins, and cysteine proteases. The insoluble carbohydrates in soybeans consist of the complex polysaccharides cellulose, hemicellulose, and pectin. The majority of soybean carbohydrates are considered dietary fiber. Soluble carbohydrates such as disaccharides are present in lower amounts and include sucrose, raffinose, and stachyose.

Three kinds of soybean flour are commercially available: Natural (or full-fat soybean flour), which contains all of the natural oils; low-fat soybean flour, which contains about one third of the natural oils; and defatted soybean flour, which has 99% of the oils removed during processing. Each type is usually heated or roasted at some stage(s) of preparation to improve palatability and flavor. Defatted soy flour is higher in protein content, close to 50 percent, and contains fewer calories per serving than natural soybean flour. The use of natural, low-fat and defatted soybean flour in the methods described herein is specifically contemplated. In addition, the use of other soy products such as soy protein concentrate (low-fat or defatted soybean flour without the soluble carbohydrates) and soy protein isolate (typically 90% soy protein by dry weight) are also contemplated.

In another aspect, the ingestible sorbing material is a phenolic compound. In some embodiments, the phenolic compound is selected from the group consisting of an anthocyanin and a proanthocyanidin. Without wishing to be bound to any particular theory, it appears that the sorption of proteins from a comestible fluid is based on the ability of several types of phenolic compounds present in plants, such as cranberry phenolic compounds, to precipitate soluble proteins resulting in the formation of insoluble protein phenolic complexes. Again, without being bound to any particular theory, it appears that the phenolic compounds precipitate soluble proteins, at least in part, by crosslinking them into larger, less soluble complexes.

The ingestible sorbing material is combined with the comestible fluid by any means known in the art to form an admixture. The term "admixture" as used herein refers to a composition produced by mixing or commingling a comestible fluid with an ingestible sorbing material. In one embodiment, the combining step comprises a method selected from the group consisting of mixing, contacting, and/or putting together the ingestible sorbing material with comestible fluid.

In another embodiment, the combining step further comprises straining the comestible fluid (e.g., plant juice) and ingestible sorbing material (e.g., ground edible material) mixture through a filter that retains the sorbing material. It is recognized that bringing the ingestible sorbing material (e.g., ground edible material) into contact with one or more comestible fluids (e.g., plant juices) will result in some sorption of sorbable natural products, leading to partial or complete conversion of the ingestible sorbing material (e.g., ground edible material) to an enriched substance, as those terms are defined and used herein.

In one embodiment, ground edible material and plant juice are combined at an exemplary ratio of about 5 g/L to about 100 g/L, ground edible material to a volume of plant juice of about 50 mL to about 100 mL. In another embodiment, a ratio from about 30 g/L to about 100 g/L ground edible material to about 50 mL to about 100 mL of plant juice is used. In yet another embodiment, a ratio of about 5 g/L, about 10 g/L, about 20 g/L, about 30 g/L, about 40 g/L, about 50 g/L, about 60 g/L, about 70 g/L, about 80 g/L, about 90 g/L, about 100 g/L, about 110 g/L, about 120 g/L, about 130 g/L, about 140 g/L, about 150 g/L, about 160 g/L, about 170 g/L, about 180 g/L about 190 g/L, about 200 g/L or more of the ground edible material to about 50 mL to about 100 mL of plant juice is contemplated. It should be appreciated that the amount of ground edible material and plant juice for use in the methods described herein can be easily increased to a commercial scale by one of ordinary skill in the art.

In some embodiments, phenolic compound(s) and dairy product (or plant juice containing protein) are combined at an exemplary ratio of about 1:3, volume of plant juice containing the phenolic compound(s) to the volume of dairy product (or plant juice containing protein). In other embodiments, the ratio is 1:2, 1:4, 1:5 or more volume of plant juice containing the phenolic compound(s) to the volume of dairy product (or plant juice containing protein). It should be appreciated that the amount of phenolic compound and dairy product (or plant juice containing protein) for use in the methods described herein can be easily increased to a commercial scale by one of ordinary skill in the art.

V. Enriched Substance

The term "enriched substance" as used herein refers to ingestible sorbing material (e.g., ground edible material or phenolic compound(s)) containing one or more sorbable natural products sorbed from a comestible fluid (e.g., plant juice, plant juice containing protein, dairy product, or juice obtained from a unicellular organism). The enriched substance may contain one or more of the sorbable natural products obtained from a comestible fluid described herein. In some embodiments, the sorbable natural products are adsorbed to the ingestible sorbing material.

The enriched substance produced by the methods disclosed herein can be formulated to accommodate specific combinations of sorbable natural products obtainable from plant juice in order to produce or elicit specific physiological effects. An enriched substance can be formulated to contain certain combinations of therapeutic or diagnostic agents, or combinations of nutritional supplements. For example, combinations of Ginkgo biloba and Goto kola are used for memory enhancement and can be included in an enriched substance described herein. In some embodiments, the enriched substance is useful to promote sexual potency, promote endurance, promote cardiovascular health, control fat and/or cholesterol, promote healthy joints, maintain or improve bone density, enhance cellular antioxidant capacity, control appetite, improve energy, increase endurance, promote weight loss, promote muscle enhancement, improve digestion, help prevent colds, fight infection, or enhance memory. As will be apparent to one skilled in the art, many of the exemplary categories outlined above overlap and are not mutually exclusive. Thus, enriched food products can be designed to contain an enriched substance that can bring about more than one desired physiological effect; as well as food products comprising a plurality of enriched substances providing overlapping or distinct benefits. The plurality of enriched substances in a food product comprise one or more edible materials to which the plurality of sorbable natural products sorb.

The one or more sorbable natural products of the enriched substance are at levels sufficient to affect the desired function of the body when taken regularly. Such levels are known in the art or can readily be determined by a skilled technician. It is understood that the total daily intake may be based on administration of one unit of the enriched substance, or it may be based on administration of more than one unit of the enriched substance. The amount of the one or more sorbable natural products in the enriched substance will thus vary, depending on the unit size relative to the desired daily dose.

The enriched substance can be formulated in various unit sizes depending on the amount of sorbable natural product(s) to be incorporated therein and on requirements of the recipient animal or target consumer. In some embodiments, the enriched substance is formulated to have a unit size between about 2 grams and about 30 grams. In another embodiment, a unit of the enriched substance is between about 3 grams and about 20 grams. In another embodiment, a unit of the enriched substance is between about 3 grams and about 15 grams. In another embodiment, a unit of the enriched substance is between about 3 grams and about 10 grams. Where appropriate, the enriched substance can be provided in a multi-dose format that is pre-scored into unit doses.

One of ordinary skill in the art will appreciate that the amount of one or more sorbable natural products obtainable from plant juice contained in the enriched substance will be dependent on the type of sorbable natural product(s) and the requirements of the target consumer. For example, the recommended dosage of a sorbable natural product, such as a vitamin, is generally less, on a weight-to-weight basis, than the recommended dosage of a macro-nutrient, such as calcium, or nutritional supplements such as creatine, protein or fiber, which are known to be required in higher amounts in order to provide a physiological effect.

In some embodiments, it will be beneficial to quantify the amount of a sorbable natural product extractable from plant juice contained in the enriched substance. Quantification can be determined by methods well known in the art including, but not limited to, high performance liquid chromatography (HPLC), HPLC-photodiode array detection (PDA), HPLC-mass spectrometry (MS) and the pH differential method.

In one embodiment, the total amount of sorbed natural product(s) constitute less than about 25% by weight of the enriched substance. In another embodiment, total amount of sorbed natural product(s) constitute between about 0.01% and about 20% by weight of the enriched substance. In another embodiment, the sorbed natural product(s) constitute between about 0.01% and about 15% by weight of the enriched substance. In another embodiment, the sorbed bioactive natural product(s) constitute between about 0.01% and about 10% by weight of the enriched substance.

In an alternative embodiment, the total amount of the sorbed natural product(s) constitutes between about 5% and about 50% by weight of the enriched substance. In another embodiment, the total amount of the sorbed natural product(s) constitutes between about 7% and about 50% by weight of the enriched substance. In a further embodiment, the total amount of the sorbed natural product(s) constitutes between about 10% and about 50% by weight of the enriched substance. In yet another embodiment, the total amount of sorbed natural product(s) constitute at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 49%, about 50% by weight or more of the enriched substance.

In some embodiments, the enriched substance is tested for efficacy in vivo. Typically, when such testing is conducted, efficacy is assessed by physiological effect or bioavailability studies using standard techniques in the pharmaceutical art, such as peak plasma levels and pharmacokinetic analyses (see, for example, Enna, et al., Current Protocols in Pharmacology, J. Wiley & Sons, New York, N.Y.).

Bioavailability studies are usually conducted by administering to groups of subjects various doses of the enriched substance under study over a pre-determined period of time and comparing plasma levels of the sorbable natural products in these groups at varying intervals with an appropriate control or controls. Appropriate controls include groups of subjects drinking unprocessed fruit juice. The subjects may or may not have fasted prior to administration of the doses of the enriched substance. Single dose or multiple dose studies may be conducted. The studies can also be used to monitor any side-effects of the dosing regimens of the enriched substance under investigation by compiling reports of any adverse effects encountered during the course of the study and comparing them to side-effects reported by the control group(s). Optionally, optimal dosing schedules can also be determined in this manner.

Studies to determine whether the combination of sorbed natural product(s) in an enriched substance bring about the desired effect in a subject can also be conducted in a manner similar to the bioavailability studies described above. Such studies are routine in the art and can be readily designed and conducted by a skilled technician. End effects measurements are dependent on the type of effect the enriched substance is intended to bring about. For example, for weight loss applications, the body weight and/or body fat percentage of individual subjects to whom varying doses of the enriched substance is being administered can be monitored over a period of time and compared to that of individuals in control groups, for example, placebo groups or groups drinking unprocessed plant juice alone.

VI. Liquor

The liquor, in some embodiments, is further processed to concentrate the non-sorbable natural products after being in contact with the ingestible sorbing material (e.g., ground edible material or phenolic compound(s)). The non-sorbable natural products are, in some embodiments, used as natural sweeteners, food coloring or food dyes.

The non-sorbable natural products may be processed or purified from the liquor through techniques known in the art, including but not limited to physical processes, fermentation, and enzymolysis. Appropriate processes and purification techniques include, but are not limited to, absorption, adsorption, agglomeration, centrifugation, chopping, cooking (baking, frying, boiling, roasting), cooling, cutting, chromatography, coating, crystallization, digestion, drying (spray, freeze drying, vacuum), evaporation, distillation, electrophoresis, emulsification, encapsulation, extraction, extrusion, filtration, fermentation, grinding, infusion, maceration, microbiological processing (rennet, enzymes), mixing, peeling, percolation, refrigeration/freezing, squeezing, steeping, washing, heating, mixing, ion exchange, lyophilization, osmosing, precipitation, salting out, sublimation, ultrasonic treatment, concentration, flocculation, homogenization, reconstitution and enzymolysis (using enzymes found in nature).

VII. Use of the Enriched Substance and Plant Liquor

In some embodiments, an enriched substance or liquor produced by the methods described herein are incorporated into consumer products. Consumer products are products available for purchase and/or use by individual consumers and include food products (including, but not limited to, enriched food products (see below), dietary supplements (see below) and medical foods (see below), cosmetic products and other personal care products. In addition, the enriched substance may be formulated into a pharmaceutical product.

A. Enriched Food Products

In some embodiments the enriched substance is incorporated into a food product to produce an enriched food product. The term "food product" as used herein refers to any substance containing nutrients that can be ingested by an organism to produce energy, promote health and wellness, stimulate growth, and maintain life. In one embodiment, the enriched substance produced by the methods described herein is used in the preparation of enriched food products comprising high amounts of concentrated sorbable natural products obtainable from plant juice separated from non-sorbable natural products (e.g., carbohydrates, sugars, fats, and oils). The term "enriched food product" as used herein refers to a food product that has been modified to include the enriched substance described herein, which provides a benefit such as a health/wellness-promoting and/or disease-preventing/mitigating/treating property beyond the basic function of supplying nutrients. Such enriched food products deliver an effective dose of the sorbable natural products obtainable from plant juice in a few servings. Drinking the original plant juices to obtain the equivalent amount of sorbed natural products provided in the enriched substance may be impossible or impractical because of the large volumes that would have to be consumed, high amounts of associated calories, and undesirable health effects associated with ingesting high-calorie sugars, carbohydrates, and other structural chemicals.

Thus, a method of making an enriched food product comprising one or more concentrated sorbable natural products obtainable from plant juice is also provided herein. Such a method comprises combining the juice with a ground edible material to form an admixture containing an enriched substance comprising the sorbed natural products; separating the enriched substance from the juice, thereby concentrating the sorbable natural products from the juice in edible form; and incorporating the enriched substance into a food product, thereby making an enriched food product comprising the concentrated sorbable natural products obtainable from plant juice.

The enriched substance can be incorporated into any food product. Exemplary food products include, but are not limited to, baked goods (cakes, cookies, crackers, breads, scones and muffins), dairy-type products (including but not limited to cheese, yogurt, custards, rice pudding, mousses, ice cream, frozen yogurt, frozen custard), desserts (including, but not limited to, sherbet, sorbet, water-ices, granitas and frozen fruit purees), spreads/margarines, pasta products and other cereal products, meal replacement products, nutrition bars, trail mix, granola, beverages (including, but not limited to, smoothies, water or dairy beverages and soy-based beverages), and breakfast type cereal products such as oatmeal. For beverages, the enriched substance (or isolated non-sorbable natural products) may be in solution, suspended, emulsified or present as a solid.

In one embodiment, the enriched food product is a meal replacement product. The term "meal replacement product" as used herein refers to an enriched food product that is intended to be eaten in place of a normal meal. Nutrition bars and beverages that are intended to constitute a meal replacement are types of meal replacement products. The term also includes products which are eaten as part of a meal replacement weight loss or weight control plan, for example snack products which are not intended to replace a whole meal by themselves, but which may be used with other such products to replace a meal or which are otherwise intended to be used in the plan. These latter products typically have a calorie content in the range of from 50-200 kilocalories per serving.

In another embodiment, the food product is a dietary supplement. The term "dietary supplement" as used herein refers to a substance taken by mouth that contains a "dietary ingredient" intended to supplement the diet. The term "dietary ingredients" includes, but is not limited to, the sorbable natural products as defined herein as well as vitamins, minerals, herbs or other botanicals, amino acids, and substances such as enzymes, organ tissues, glandulars, and metabolites.

In yet another embodiment, the food product is a medical food. The term "medical food" as used herein means a food which is formulated to be consumed or administered entirely under the supervision of a physician and which is intended for the specific dietary management of a disease or condition for which distinctive nutritional requirements, based on recognized scientific principles, are established by medical evaluation.

B. Food Additives

In some embodiments, the plant liquor (or non-sorbable natural products isolated from the plant liquor) are incorporated within (or added to) a food product to improve the palatability, flavor or color of the food product.

In some embodiments, the plant liquor is subsequently processed to concentrate the non-sorbable natural products from the plant liquor to produce sweet-tasting food additives (e.g., natural sweeteners and syrups), flavorings and colorings. The concentration step, in some embodiments, comprises evaporation under vacuum with or without heat, boiling, sun- or heat-drying, freeze-drying, spray drying, reverse osmosis or other known methods of concentrating substances in liquids.

The term "natural sweetener" as used herein refers to any substance originating in nature that when added to a food or beverage sweetens the taste of the food or beverage.

The terms "food coloring" or "food dye" as used herein is any substance that when added to food or drink changes the color of the food or drink. Exemplary food colorings obtainable from the non-sorbable natural products include, but are not limited to, caramel coloring (obtained from caramelized sugar), annatto (a reddish-orange dye made from the seed of the achiote), chlorophyll (green dye typically made from chlorella algae), betanin (a red dye extracted from beets), turmeric (obtained from curcuminoids), paprika, saffron (obtained from carotenoids), pandan and butterfly pea.

To ensure reproducibility, the colored components of these substances are often provided in highly purified form, and for increased stability and convenience, the colored components are, in some embodiments, formulated in suitable carrier materials (solid and liquids).

C. Cosmetic Applications

In some embodiments, the enriched substance or natural products isolated from the enriched substance are useful as cosmeceuticals. The term "cosmeceutical" as used herein means an ingredient for a cosmetic, body care or hair care personal product having a positive effect on the physical condition of the body (e.g., the skin, the nails or hair). In some embodiments, enriched substances containing sorbable natural products having antioxidant properties (e.g., anthocyanins and resveratrol) would be useful for cosmetic (or personal care) applications in which the inclusion of antioxidants is desired. For example, in such embodiments, the enriched substance (or isolated natural products from the enriched substance) is incorporated into a cosmetic composition for conditioning, moisturizing and smoothening human skin and preventing or reducing the appearance of lined, wrinkled or aged skin. In some embodiments, enriched substances containing other sorbable natural products (including, but not limited to, quercetin, 3-hydroxyflavone, azaleatin, fisetin, galangin, gossypetin, kaempferide, kaempferol, isohamnetin, morin, myricetin, natsudaidain, pachypodol, rhamnazin, rhamnetin, astragalin, azalein, hyperoside, isoquercitin, kaempferitin, myricitrin, quercitrin, robinin, rutin, spiraeoside, xanthorhamnin, amuirensin, icariin, troserutin, fisetinidol, robinetinidol, epicatechin, mesquitol, epigallocatechin, epicatechin gallate, epigallocatechin gallate, butin, eriodictyol, hesperetin, homoeriodictyol, isosakuranetin, naringenin, pinocembrin, sakuranetin, sakuranin, poriol, sterubin, eriocitrin, hesperedin, liquiritin, naringin, narirutin, poncirin, nirurin, sakuranin, aurantinidin, cyanidin, 6-hydroxycyanidin, delphinidin, europinidin, luteolinidin, fisetinidin, guibourtinidin, robinetinidin, pelargonidin, lamvidin, peonidin, petunidin, 5-desoxy-malvidin, capensinidin, diosmetinidin, gesneridin, rosinidin, antirrhinin, chrysanthenin, myrtillin, tulipanin, violdelphin, malvin, oenin, primulin, pulchellidin 3-glucoside, pulchellidin 3-rhamnoside, cyanidin-3-(di-p-coumarylglucoside)-5-glucoside, commelinin, cyanosalvianin, protocyanin, protodelphion, phytoestrogen, caffeine, artemisinin, carotenoids pigments, camphor, menthol, limonene, carvone, nepetalactone, hecogenin, digitoxigenin, chicory sesquterpene lactones, triptolide, caffeine, ecdysteroids, isothiocyanates, sesquiterpene lactones, barberine, gingerols, ginsenosides, glycycrrhizin, polymethoxylated flavones, tocotrienols, glucosinolates, punicalagins, soluble dietary fiber and organosulfur compounds from onions and garlic, as well as compounds or mixtures of compounds from Echinacea extracts, saw palmetto extracts, ginkgo extracts, black cohosh extracts, St. John's wort extracts, milk thistle extracts and vitamins (including vitamin A (retinol), vitamin $B_1$ (thiamine), vitamin C (ascorbic acid), vitamin D (calciferol), vitamin $B_2$ (riboflavin), vitamin E (tocopherol), vitamin $B_{12}$ (cyanocobalamin), vitamin K (phylloquinone), vitamin $B_5$ (pantothenic acid), vitamin $B_7$ (biotin), vitamin $B_6$ (pyridoxine), vitamin $B_3$ (niacin) and vitamin $B_9$ (folic acid)) are incorporated into a cosmetic product.

In some embodiments, natural oils present in the liquor (e.g., plant liquor) can be used as a cosmeceutical. For example, natural oils, including but not limited to, almond oil, castor oil, grapeseed oil, jojoba oil, coconut oil, avocado oil, carrot oil, rice bran oil, rose hips oil, wheatgerm oil, passion flower oil, Brazil nut oil, watermelon seed oil, macadamia nut oil, starflower oil, Artemisia oil, St. John's Wort Oil (*Hypericum perforatum*), Marigold or Calendula Oil (*Calendula officinalis*) and meadowfoam seed oil would be useful in cosmetic applications wherein the conditioning, moisturizing or conditioning of the skin is desired. In some embodiments, natural compounds (e.g., anthocyanins, turmeric) present in the plant liquor or enriched substance that can be used as natural pigments for cosmetics.

Compositions suitable for personal care products generally are formulated as, e.g., shampoos, conditioners, shower gels, liquid hand cleansers, facial cleansers, moisturizers, lotions, skin lotions and creams (such as eye creams and lip creams), facial skin cosmetics (such as blusher and highlighter), eye cosmetics (such as eye shadow, eye brow color, and eye liner), lip cosmetics (such as lip rouge), foundation, concealer, wrinkle-soothing serums, mascaras, skin facial masks, sunscreens, scalp hair-styling aids, facial hair-styling aids, emulsions, oils, mousses, ointments, milks, pomades, solutions, sprays, aerosols, powders, foams, gels (such as skin gels, eye gels, and lip gels), or other skin or hair products known in the art.

D. Pharmaceutical Products.

In some embodiments, the enriched substance or natural products isolated from the enriched substance are incorporated into a pharmaceutical product or composition. Pharmaceutical compositions comprise a prophylactically or therapeutically effective amount of the enriched substance or natural products isolated from the enriched substance described herein, and typically one or more pharmaceutically acceptable carriers or excipients (which are discussed below).

VIII. Route of Administration and Dosage

The disclosure contemplates compositions comprising an enriched substance (or the enriched substance alone) that are, in some embodiments, tabletted, encapsulated or otherwise formulated for oral administration. The compositions may be provided as pharmaceutical compositions, nutraceutical compositions (e.g., a dietary supplement), or as a food or beverage additive, as defined by the U.S. Food and Drug Administration. The dosage form for the above compositions are not particularly restricted. For example, liquid solutions, suspensions, emulsions, tablets, pills, capsules, sustained release formulations, powders, suppositories, liposomes, microparticles, microcapsules, sterile isotonic aqueous buffer solutions, and the like are all contemplated as suitable dosage forms.

The compositions typically include one or more suitable diluents, fillers, salts, disintegrants, binders, lubricants, glidants, wetting agents, controlled release matrices, colorings, flavoring, carriers, excipients, buffers, stabilizers, solubilizers, commercial adjuvants, and/or other additives known in the art.

Any pharmaceutically acceptable (i.e., sterile and acceptably non-toxic as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Such compositions may influence the physical state, stability, rate of in vivo release, and rate of in vivo clearance of the functional compounds.

Pharmaceutically acceptable fillers can include, for example, lactose, microcrystalline cellulose, dicalcium phosphate, tricalcium phosphate, calcium sulfate, dextrose, mannitol, and/or sucrose. Salts, including calcium triphosphate, magnesium carbonate, and sodium chloride, may also be used as fillers in the pharmaceutical compositions.

Binders may be used to hold the composition containing the enriched substance together to form a hard tablet. Exemplary binders include materials from organic products such as acacia, tragacanth, starch and gelatin. Other suitable binders include methyl cellulose (MC), ethyl cellulose (EC) and carboxymethyl cellulose (CMC).

In some embodiments, an enriched food product comprising the enriched substance further comprises a bioavailability enhancer, which acts to increase the absorption of the sorbable natural product(s) by the body. Bioavailability enhancers can be natural or synthetic compounds. In one embodiment, the enriched food product comprising the enriched substance further comprises one or more bioavailability enhancers in order to enhance the bioavailability of the bioactive natural product(s).

Natural bioavailability enhancers include ginger, caraway extracts, pepper extracts and chitosan. The active compounds in ginger include 6-gingerol and 6-shogoal. Caraway oil can also be used as a bioavailability enhancer (U.S. Patent Application 2003/022838). Piperine is a compound derived from pepper (*Piper nigrum* or *Piper longum*) that acts as a bioavailability enhancer (see U.S. Pat. No. 5,744,161). Piperine is available commercially under the brand name Bioperine® (Sabinsa Corp., Piscataway, N.J.). In some embodiments, the natural bioavailability enhancers is present in an amount of from about 0.02% to about 0.6% by weight based on the total weight of enriched food product.

Examples of suitable synthetic bioavailability enhancers include, but are not limited to, Gelucire®, Labrafil® and Labrasol®, Lauroglycol®, Pleurol Oleique® (Gattefosse Corp., Paramus, N.J.) and Capmul® (Abitec Corp., Columbus, Ohio).

The amount and administration regimen of the enriched substance is based on various factors relevant to the purpose of administration, for example human or animal age, sex, body weight, hormone levels, or other nutritional need of the human or animal. In some embodiments, the enriched substance is administered to an animal in an amount from about 0.001 mg/kg body weight to about 10 g/kg body weight. In some embodiments, the enriched substance is administered to an animal in an amount of about 0.005 mg/kg body weight. In some embodiments, the enriched substance is administered to an animal in an amount of about 0.01 mg/kg body weight. In some embodiments, the enriched substance is administered to an animal in an amount of about 0.05 mg/kg body weight. In some embodiments, the enriched substance is administered to an animal in an amount of about 0.1 mg/kg body weight. In some embodiments, the enriched substance is administered to an animal in an amount of about 1 mg/kg body weight. In some embodiments, the enriched substance is administered to an animal in an amount of about 10 mg/kg body weight. In some embodiments, the enriched substance is administered to an animal in an amount of about 100 mg/kg body weight. In some embodiments, the enriched substance is administered to an animal in an amount of about 250 mg/kg body weight. In some embodiments, the enriched substance is administered to an animal in an amount of about 500 mg/kg body weight. In some embodiments, the enriched substance is administered to an animal in an amount of about 1 g/kg per body weight. In some embodiments, the enriched substance is administered to an animal in an amount of about 2.5 g/kg body weight. In some embodiments, the enriched substance is administered to an animal in an amount of about 5 g/kg body weight. In some embodiments, the enriched substance is administered to an animal in an amount of about 7.5 g/kg body weight. In some embodiments, the enriched substance is administered to an animal in an amount of about 10 g/kg body weight.

A typical regimen may comprise multiple doses of an enriched substance. In one embodiment, the enriched substance is administered once per day. The enriched substance may be administered to an individual at any time. In some embodiments, the enriched substance is administered concurrently, or prior to or at the consumption of a meal.

It will be appreciated that the enriched substance described herein is useful in the fields of human medicine and veterinary medicine to provide concentrated sorbable natural products obtainable from a comestible fluid (e.g., plant juice, dairy product, or from the juice of a unicellular organism) to a subject in need thereof. Thus, the subject or individual to be treated may be a mammal, such as a human. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The properties of the enriched food products disclosed herein comprising the enriched substance ensure that the foods are easy to take and/or to administer. In one embodiment, the enriched substance is formulated for administration to humans and thus contain flavors that would appeal to humans, such as fruit-based flavors. An enriched substance that is formulated with confectionery-like qualities and flavors is also appealing to children who are often resistant to taking medications or supplements due to unpleasant tastes or texture. Thus, in another embodiment, the enriched substance provides a means of easily providing natural products obtainable from plant juice to children.

In another embodiment, the enriched substance is formulated for administration to a non-human animal. Administration of sorbable natural products obtainable from plant juice to an animal in conventional solid dosage forms, such as tablets and capsules, can be problematic in that the animal often expels them, and multiple dosing is often difficult because the animal learns to resist the dosing procedure. It will be readily apparent that the enriched substance, formulated as an enriched food product, is ideally suited for administration of sorbable natural products obtainable from plant juice to animals. When formulated for this purpose, the enriched food product comprising the enriched substance may contain flavors that more typically appeal to non-human animals, for example, fish or meat flavors.

EXAMPLES

The following Examples are provided to describe the invention in greater detail, and are intended to illustrate, not to limit, the appended claims. Example 1 is a comparison of different plant flours as sorbers of anthocyanins from blueberry juice. Example 2 is a comparison of different soy-based ground edible materials as sorbers of anthocyanins from blueberry juice. Example 3 demonstrates that incubation time does not affect the amount of anthocyanins in blueberry juice that to sorb to soybean flour. Example 4 demonstrates that soybean flour at varying concentrations sorbs anthocyanins from blueberry juice. Example 5 demonstrates that soybean flour does not sorb glucose present in blueberry juice and grape juice. Example 6 discloses that anthocyanins are sorbed by soybean flour from blueberry juice after three rounds of soybean flour treatment. Example 7 demonstrates that soybean flour at varying concentrations effectively sorbs anthocyanins from grape juice. Example 8 demonstrates the acute hypoglycemic effect of anthocyanin-fortified soybean flour in a diabetic mouse model. Example 9 demonstrates that soybean flour at varying concentrations sorbs resveratrol from grape juice. Example 10 demonstrates that soybean flour at varying concentrations sorbs quercetin from grape juice. Example 11 demonstrates that soybean flour at varying concentrations sorbs catechins and caffeine from green tea. Example 12 demonstrates that soybean flour sorbs 6-gingerol. Example 13 demonstrates that soybean flour sorbs multiple sesquiterpene lactones from a chicory root extract. Example 14 demonstrates that the sorbed natural products in the enriched substance can be eluted from the solid for use in the absence of the ground edible material matrix. Example 15 demonstrates that carotenoids from carrot juice are found in the plant liquor rather than sorbing to the ground edible material in the form of plant flour. Example 16 demonstrates that the methods described herein are useful for the preparation of plant liquors comprising non-sorbable natural products (such as fructose, glucose, and sucrose), which can be further processed to produce natural sweeteners and flavoring. Example 17 identifies various natural products present in the enriched substance and plant liquor prepared from blueberry juice. Examples 18-21 demonstrate that phenolic compounds present in cranberry juice concentrate are capable of sorbing (or forming complexes with) soluble proteins present in various plant juices. Example 22 demonstrates that phenolic compounds present in cranberry juice concentrate are capable of sorbing (or forming complexes with) soluble proteins present in milk.

Example 1. Comparison of Different Ground Edible Materials as Sorbers of Anthocyanins From Blueberry Juice Different types of ground edible materials were tested to determine which, if any, could sorb (e.g., adsorb) and concentrate compounds known for their health/nutritional value (e.g., anthocyanins). Full-fat soybean flour (Hodgson Mill Inc., IL), defatted soybean flour (Hodgson Mill Inc., IL), white whole-wheat flour (King Arthur Flour Company, Inc), corn meal (Goya Foods, Inc.), brown rice flour (Arrowhead Mills), and blueberry juice (R. W. Knudsen) were all purchased from a local grocery store. Each flour was separately added to blueberry juice at a concentration of 5 g/L in a volume of 50 ml of the blueberry juice and mixed at room temperature for five minutes on a magnetic stir plate. The mixture was then centrifuged for 15 minutes at 15,000 rpm (Beckman, JA-17 rotor) and the decanted supernatant was subsequently filtered through a 0.22 µm syringe filter to further remove any particulate material that could interfere with the anthocyanin quantification step. The concentration of total monomeric anthocyanins in untreated and flour-treated blueberry juice was determined using the Association of Official Analytical Chemistry (AOAC) pH differential method (absorbance at 520 nm and 700 nm) adapted to a 96-well format.

Monomeric anthocyanin pigments reversibly change color with change in pH, with the colored oxonium form present at pH 1 and the colorless hemiketal form present at pH 4.5. Degraded anthocyanins in the polymeric form are resistant to color changes and absorb light at both pH 1 and 4.5. Therefore, they are subtracted out when calculating the anthocyanin concentration. Juice samples were diluted in pH 1 buffer (0.025 M KCl) or pH 4.5 buffer (0.4 M $CH_3CO_2Na.3H2O$) and the absorbance of each sample was measured at 520 nm and 700 nm against a water control. The absorbance of monomeric anthocyanins was calculated as follows: $(Abs_{520}-Abs_{700})_{pH\ 1}-(Abs_{520}-Abs_{700})_{pH4.5}$. Further calculation of the monomeric anthocyanin concentration in juice (mg/L) was based on cyanidin 3-glucoside (molar extinction coefficient ε=26,900; molecular weight 449.2 g/mol) equivalents. The difference in anthocyanin concentration between untreated and flour-treated juice samples was used to determine the concentration of anthocyanins bound to the flour.

Results indicated that approximately 4 mg/g anthocyanin was bound to the soybean flour. See Table 1 below. Results further indicated that the defatted soybean flour (5 g/L) sorbed approximately 30% of anthocyanins from the blueberry juice sample (50 mL).

Anthocyanins also bound to other flours tested (i.e., white whole wheat flour, corn meal and brown rice flour), but to a lesser extent than the soybean flour (approximately 3 mg/g, 2.7 mg/g and 1.8 mg/g, respectively).

TABLE 1

| Matrix (5 g/L) | Concentration of anthocyanin sorbed to matrix (mg/g) | % anthocyanin sorbed |
|---|---|---|
| Defatted Soybean Flour | 4.2 | 29 |
| Whole Wheat Flour | 3.0 | 21 |
| Corn Flour | 2.7 | 19 |
| Brown Rice Flour | 1.8 | 12 |

The experiment was repeated with additional ground edible materials (i.e., wheat bran (Shiloh Farms, Ariz.), oat bran (Bob's Red Mill, OR) and cellulose (Research Diets, NJ)) to determine which, if any, could sorb (e.g., adsorb) and concentrate compounds known for their health/nutritional value (e.g., anthocyanins). Defatted soybean flour was again used as a positive control. Each material was separately added to blueberry juice concentrate (Oxford Frozen Foods) at a concentration of 100 g/L in a volume of 50 ml of the blueberry juice and mixed at room temperature for five minutes on a magnetic stir plate. The juice samples were separated from the ground edible material as described above and anthocyanin concentrations were determined using the pH differential method.

Results indicated that anthocyanins sorbed to wheat bran, oat bran and cellulose, but to a lesser extent than the soybean flour (approximately 3.5 mg/g, 1.8 mg/g and 2.6 mg/g, respectively). See Table 2.

TABLE 2

| Matrix (100 g/L) | Concentration of anthocyanin sorbed to matrix (mg/g) | % anthocyanin sorbed |
|---|---|---|
| Defatted Soybean Flour | 4.3 | 56 |
| Wheat Bran | 3.5 | 45 |
| Oat Bran | 1.8 | 26 |
| Cellulose | 2.6 | 32 |

The experimental results establish that a variety of ground edible materials successfully sorbed anthocyanins from a plant juice (blueberry juice).

Example 2. Sorption of Anthocyanins from Blueberry Juice to Different Soybean Products Blueberry juice (R. W. Knudsen) was mixed for 5 minutes with full-fat soybean flour (Hodgson Mill Inc., IL) low-fat soybean flour (Harvest Inovations, IA), defatted soybean flour (Hodgson Mill Inc., IL), soy protein concentrate (ADM), or soy protein isolate (GNC) at a concentration of 5 g/L in a total volume of 50 ml. As described in Example 1, juice samples were separated from the flour and anthocyanin concentrations were determined using the pH differential method. The anthocyanin concentrations from untreated and treated juice samples were used to calculate the total amount and percentage of anthocyanins sorbed by the different soy matrices. The results (approximate) are set forth below in Table 3. In general, increasing protein concentration in the soy matrix positively correlated with increased ability to sorb anthocyanins from the juice. Full-fat soybean flour contained the least amount of protein (33%) and sorbed the least amount of anthocyanins from the juice (3.7 mg/g), while soy protein isolate with the greatest amount of protein (85%) sorbed the highest amount of anthocyanins (5.3 mg/g).

TABLE 3

| Matrix (100 g/L) | Protein (%) | Concentration of anthocyanin sorbed to matrix (mg/g) |
|---|---|---|
| Full Fat Soybean Flour | 33 | 3.7 |
| Low Fat Soybean Flour | 53 | 4.4 |
| Defatted Soybean Flour | 47 | 4.8 |
| Soy Protein Concentrate | 70 | 5.1 |
| Soy Protein Isolate | 83 | 5.3 |

The experimental results demonstrate that increased protein concentration in the ground edible materials results in an increased concentration of anthocyanins sorbed to the ground edible material.

Example 3. Concentration of Anthocyanins from Blueberry Juice Bound to Soybean Flour as a Function of Incubation Time Soybean flour at a concentration of 30 g/L was added to 50 mL of blueberry juice and mixed at room temperature for 5, 10, 15, and 30 minutes on a magnetic stir plate. As described in Example 1, the flour was separated from the juice and the concentration of anthocyanin sorbed (e.g., adsorbed) to the soybean flour was determined. Increasing the incubation time did not significantly increase the concentration of anthocyanins sorbed by the soybean flour.

The experiment was repeated as follows. Soybean flour at a concentration of 100 g/L was added to 50 mL of diluted blueberry juice concentrate and mixed at room temperature for 5, 15, 30 and 60 minutes on a magnetic stir plate. Triplicate samples were used for each time point. The flour was separated from the juice as described in Example 1 and the amount of anthocyanins sorbed to the soybean flour was determined (measured as a mass of anthocyanin sorbed per unit mass of soybean flour). The results were similar to the previous experiment in that increasing the incubation time did not significantly increase the concentration of anthocyanins sorbed by the boybean flour. See Table 4.

TABLE 4

| Time (minutes) | Concentration of anthocyanin sorbed to soybean flour (100 mg/g) |
|---|---|
| 5 | 8.1 ± 0.3 |
| 15 | 8.1 ± 0.1 |
| 30 | 8.4 ± 0.2 |
| 60 | 8.1 ± 0.7 |

The data disclosed in this Example establish that sorption (e.g., adsorption) of natural products from plant juice to plant flour occurs rapidly, a significant benefit for commercial-scale operations.

Example 4. Anthocyanin Adsorption from Blueberry Juice

Soybean flour at concentrations of 5, 10, 30, 50, and 100 g/L were added separately to 50 mL of blueberry juice and mixed at room temperature for five minutes. As described in Example 1, juice samples were separated from the flour and anthocyanin concentrations were determined. The anthocyanin concentrations of untreated and flour-treated juice samples were used to calculate the total amount and percentage of anthocyanins sorbed (e.g., adsorbed) to increasing amounts of soybean flour. The results (approximate) are set forth below in Table 5. Increasing the concentration of flour mixed with blueberry juice significantly increased the percentage of anthocyanin from the juice that could be sorbed by the soybean flour. As expected, the amount of anthocyanin sorbed to the soybean flour was directly proportional to the concentration of soybean flour added to the juice. The experiment demonstrates the routine procedure required to optimize the amount of plant flour, or concentration thereof, to use in sorbing one or more natural products from plant juices to one or more plant flours.

After mixing soy flour with blueberry juice, followed by centrifuging and decanting the juice supernatant, the wet paste of soy flour containing the sorbed anthocyanins was freeze-dried to obtain anthocyanin-enriched soy flour. Anthocyanins sorbed (e.g., adsorbed) to the soybean flour were eluted from the flour with acidic methanol. The concentration of anthocyanins eluted from the soy flour can be determined using the pH differential method and based on the original concentration of anthocyanins bound to the soy flour, recovery is about 100%.

TABLE 5

| Soybean flour (g/L) | Concentration of anthocyanin bound to soybean flour (mg/g) | % anthocyanin sorbed by soybean flour |
|---|---|---|
| 5 | 3.4 | 17 |
| 10 | 3.2 | 33 |
| 30 | 1.6 | 51 |
| 50 | 1.1 | 59 |
| 100 | 0.6 | 59 |

Example 5. Effect of Soybean Flour on Glucose Concentration in Blueberry and Grape Juices Soybean flour at concentrations of 5, 10, 30, 50, and 100 g/L were separately added to 50 mL of either blueberry juice or Concord grape juice (Santa Cruz Organic®) and mixed at room temperature for five minutes. As described in Example 1, the flour was separated from the juice and the concentration of glucose in both untreated and flour-treated juice samples was quantified using the QuantiChrom™ Glucose assay kit (BioAssay Systems). Glucose reacts with o-toluidine in glacial acetic acid to produce N-glucosylamine, which is blue-green in color and can be measured spectrophotometrically. The intensity of absorbance at 630 nm is proportional to glucose concentration. The concentration of glucose in juice samples was quantified against a standard curve of glucose. The results are provided below in Table 6.

TABLE 6

| Soybean flour (g/L) | Concentration of glucose remaining in blueberry juice (mg/ml) | Concentration of glucose remaining in grape juice (mg/ml) |
|---|---|---|
| 0 | 55.7 | 71 |
| 5 | N/A | 71 |
| 10 | 57.65 | 69 |
| 30 | 56.16 | 70 |
| 50 | 58.11 | 78 |
| 100 | 54.83 | 76 |

Results indicated that the glucose concentrations of untreated juice and juice treated with increasing amounts of soybean flour were not significantly different, confirming that glucose present in both the blueberry juice and grape juice sorbed (e.g., adsorbed) poorly or not at all to the flour.

These results demonstrate the selective sorption (e.g., adsorption) properties of plant flours when contacted by plant juices and further demonstrates that glucose remains in the plant liquor. The selective sorption (e.g., adsorption) yields a solid enriched with natural products beneficial to consuming animals while avoiding calorie-rich sugars.

Example 6. Anthocyanins Sorbed by Soybean Flour by Three Successive Exposures to Blueberry Juice/Blueberry Plant Liquor Soybean flour at concentrations of 5, 10, and 30 g/L were separately added to 50 mL of blueberry juice and mixed at room temperature for five minutes on a magnetic stir plate. After the juice samples were separated from the flour, an aliquot of juice filtrate was reserved for the quantification of anthocyanins and additional soybean flour at the same concentrations was mixed with the remainder of the juice. After five minutes, juice was separated from the soybean flour and subjected to a third round of soybean flour treatment, again using the same concentrations of soybean flour. The concentration of anthocyanins sorbed (e.g., adsorbed) by the soybean flour after each round of flour treatment, as well as the percentage of anthocyanin that was sorbed in each successive round of soybean flour treatment, was determined. The results (in approximate values) are set forth below in Table 7.

TABLE 7

| Soybean flour (g/L) | Concentration of anthocyanin bound to soybean flour (mg/g) | % anthocyanin sorbed by soybean flour |
|---|---|---|
| Round 1 | | |
| 5 | 3.3 | 17 |
| 10 | 2.5 | 16 |
| 30 | 1.4 | 10 |
| Round 2 | | |
| 5 | 2.5 | 26 |
| 10 | 1.5 | 21 |
| 30 | 0.3 | 14 |
| Round 3 | | |
| 5 | 1.4 | 44 |
| 10 | 0.8 | 17 |
| 30 | 0.1 | 6 |

The data indicate that multiple rounds of adsorption may result in useful enriched substances and provide another routine approach to optimizing the adsorption process (e.g., by optimizing the rounds of adsorption for a given ration of plant juice to plant flour or by revealing the saturation point of sorbing flour for a given plant juice quantity.

Example 7. Adsorption of Anthocyanins from Concord Grape Juice by Soybean Flour Concord (red) grape juice (Santa Cruz Organic®) was purchased from a local grocery store. Soybean flour at concentrations of 10, 30, 50, and 100 g/L were separately added to 50 mL grape juice and mixed at room temperature for five minutes. As described in Example 1, juice samples were separated from the flour and anthocyanin concentrations were determined using the pH differential method. The anthocyanin concentrations from untreated and flour-treated juice samples were used to calculate the total amount and percentage of anthocyanins sorbed (e.g., adsorbed) to increasing amounts of soybean flour. The results (approximate) are set forth below in Table 8.

TABLE 8

| Soybean flour (g/L) | Concentration of anthocyanin bound to soybean flour (mg/g) | % anthocyanin sorbed by soybean flour |
|---|---|---|
| 10 | 5.5 | 32 |
| 30 | 3.0 | 54 |
| 50 | 2.2 | 65 |
| 100 | 1.2 | 71 |

This experiment was repeated and the results are provided below in Table 9.

TABLE 9

| Soybean flour (g/L) | Concentration of anthocyanin bound to soybean flour (mg/g) | % anthocyanin adsorbed by soybean flour |
|---|---|---|
| 5 | 8.4 | 30 |
| 10 | 5.0 | 36 |
| 30 | 2.5 | 55 |
| 50 | 1.8 | 64 |
| 100 | 1.0 | 74 |

Increasing the amount of flour mixed with grape juice significantly increased the percentage of anthocyanin from the juice that could be sorbed by the soybean flour. As expected, the concentration of anthocyanin in the soybean flour was inversely proportional to the concentration of soybean flour added to the juice, reflecting progressively diminishing returns with increasing relative quantities of the ground edible material per unit plant juice. The results are consistent with the results presented in Example 6 and show that optimization of plant juice to plant flour ratios are determinable by routine procedures. This Example also demonstrates the consistency of the amount of anthocyanins sorbed to the ground edible material by a given relative quantity of ground edible material.

Example 8. Acute Hypoglycemic Effect of Anthocyanin-Fortified Soybean Flour in C57/BL6 DIO Mice 6 Hours after Gavage This experiment was performed to determine whether blueberry anthocyanin-enriched soybean flour (SF) is effective in reducing blood glucose in diabetic animals. Soybean flour at 30 g/L was incubated with 100 mL of blueberry juice (BBJ) for five minutes, separated by filtration as described in Example 1, and dried at 45° C. for 2 days.

Five-week-old male C57bl/6J mice (10-20 g) were acclimatized for one week before being randomly assigned into experimental groups. During the acclimatization period, the animals were fed a regular diet ad libitum. Six-week-old mice were placed on a very high-fat diet (VHFD) for a 12-week period, which led to the development of insulin resistance and hyperglycemia. Thereafter, animals were randomly divided into experimental groups (n=5), fasted for four hours, and fed orally (gavaged) with 300 or 600 mg/kg of BBJ-SF (i.e., enriched substance) in 75% Labrasol or vehicle (75% Labrasol). Blood glucose readings were made 6 hours after treatment (other than the gavage, animals were fasted during the testing period). As a positive control, metformin was administered to a group of animals at a dose of 300 mg/kg using the same vehicle (n=5±SD; *: $p<0.05$; : $p<0.01$; *: $p<0.001$). Results indicated that the blueberry anthocyanin enriched-soybean flour (300 mg/kg; $p<0.01$; or 600 mg/kg; $p<0107$)) significantly reduced blood glucose levels in diabetic animals, similar to the positive control.

The results establish that plant flours enriched with natural products, such as the anthocyanins in blueberry juice, are therapeutically useful, for example, in providing a low-cost, effective treatment for diabetes mellitus.

Example 9. Adsorption of Resveratrol from Grape Juice by Soybean Flour

Soybean flour (30 g/L) was added to 50 mL of Concord grape juice and mixed at room temperature for five minutes. The juice was separated from the flour by centrifugation and then filtered through a 0.22 µm syringe filter. The resveratrol content of the untreated and flour-treated juice samples (n=1) was quantified by HPLC-MS according to a previously published method (Wang et al., J. Agric. Food Chem., 50:431-435, 2002, the disclosure of which is incorporated herein by reference in its entirety.).

The enriched substance was prepared as follows. Briefly, 2 ml of untreated or soybean flour-treated grape juice sample was mixed with 20 ml of methanol overnight and samples were then centrifuged at 2280 g for 5 minutes and the methanol portion was removed. The solid residue was washed with an additional 10 ml of methanol. Methanol supernatants were combined and evaporated using a rotary evaporator and the methanol-free samples were diluted in 10 ml of water for enzymatic hydrolysis with 30 mg β-D-glucosidase (2.3 units/mg). Each sample was then extracted four times with 7 ml of water-saturated ethyl acetate. Ethyl acetate extracts were combined and evaporated to dryness under vacuum using a rotary evaporator. Residues were dissolved in 1 ml of methanol/0.5% formic acid (7:3; v/v) for LC-MS analysis. Standards of resveratrol were prepared for LC-MS to generate standard curves and quantify the levels of each compound in juice samples.

Resveratrol, a polyphenol found in grape juice, is known in the art to have anti-aging properties and it is expected to exhibit anti-inflammatory, anti-cancer, blood sugar-lowering, and cardiovascular health-promoting effects.

Results of sorbing (e.g., adsorbing) natural products in Concord grape juice to plant flour are set forth below in Table 10. The initial concentration of resveratrol in the grape juice was determined to be about 2100 ng/ml. The concentration of resveratrol bound to the soybean flour was determined to be approximately 59.2 µg/g.

TABLE 10

| Sample | Resveratrol in Grape Juice (ng/ml) | Concentration of Resveratrol in SF (µg/g) | % Resveratrol Sorbed to SF |
|---|---|---|---|
| Grape Juice | 2100 | N/A | N/A |
| Grape Juice + Soybean flour (30 g/L) | 325 | 59.2 | 85 |

The experiment shows that plant flour can sorb a polyphenol in the form of resveratrol, in addition to sorbing anthocyanins. Moreover, converting units shows that the amount of sorbed or bound resveratrol was 59.2 µg per gram of soybean flour, with 30 g/L×0.05 L=1.5 g soybean flour. Thus, 59.2 µg×1.5 g=88.8 mg bound resveratrol. Given the initial resveratrol concentration of 2100 ng/mL×50 mL=105 µg resveratrol. The percentage of resveratrol in grape juice that was bound by plant flour was 88.8 µg/105 µg×100=85%, as indicated above in Table 10.

Example 10. Adsorption of Quercetin from Grape Juice by Soybean Flour

Soybean flour (30 g/L) was added to 50 mL of Concord grape juice and mixed at room temperature for five minutes. The juice was separated from the flour by centrifugation and then filtered through a 0.22 µm syringe filter. Untreated and soybean flour-treated juice samples (n=1) were processed as described in Example 8 and the quercetin content of untreated and soybean flour-treated samples was determined by HPLC-MS. Quercetin is a polyphenolic flavonoid compound. More specifically, it is a flavonol known in the art to have anti-inflammatory and antioxidant properties, and it is expected to be useful in treating cancer. Quercetin is also known to have endurance-promoting effects.

Results are set forth below in Table 11. The initial concentration of quercetin in the grape juice was determined to be approximately 1997 ng/ml. The concentration of quercetin bound to the soybean flour was determined to be approximately 49.3 µg/g.

TABLE 11

| | Quercetin in Grape Juice (ng/ml) | Concentration of Quercetin in Soybean flour (µg/g) | % Quercetin Sorbed to SF |
|---|---|---|---|
| Grape Juice | 1997 | | |
| Grape Juice + Soybean flour (30 g/L) | 519 | 49.3 | 74 |

The experiment shows that plant flour can sorb (e.g., adsorb) a polyphenol in the form of quercetin, in addition to sorbing anthocyanins.

Example 11. Sorption of Catechins and Caffeine from Green Tea by Soybean Flour Dried green tea leaves were purchased from an online vendor (English Tea Store) and a water extract was made by heating 10 g of tea in 400 ml of water at 80° C. for 30 minutes. The tea (water extract) was separated from the leaves and then mixed with increasing amounts of commercially-available defatted soybean flour for three minutes at room temperature on a magnetic stir plate. As described in Example 1, the flour was separated from the tea and the concentration of catechins sorbed (e.g., adsorbed) to the flour was determined using a vanillin-based assay described in Sun et al. (J. Agric. Food Chem., 46:4267-4274, 1998; the disclosure of which is incorporated herein by reference in its entirety). Catechins react with vanillin to yield colored complexes, while non-catechin compounds in tea extracts, such as gallic acid and caffeine, do not take part in the colorimetric reaction. Catechins, or flavonoid compounds (flavan-3-ols) are polyphenolic compounds having anti-oxidant, anti-cancer, anti-stroke, anti-heart failure, and anti-diabetic properties.

Briefly, in the vanillin-based assay, 100 µl of diluted tea samples, 250 µl of 9N $H_2SO_4$ and 250 µl of vanillin (1% (w/v) in methanol) were mixed in microfuge tubes and left at room temperature for 10 minutes, after which the absorbance of each sample was read at 500 nm in a microplate reader. A standard curve of epigallocatechin gallate (EGCG) was employed to quantify the concentration of total catechins. Therefore, total catechin concentration is expressed as EGCG equivalents.

The results (approximate) are set forth below in Table 12. Increasing the concentration of flour mixed with the tea significantly increased the percentage of catechins that could be sorbed (e.g., adsorbed) by the soybean flour. As expected, the concentration of catechins in the soybean flour was inversely proportional to the concentration of soybean flour added.

TABLE 12

| Soybean flour (g/L) | Concentration of catechin bound to soybean flour (mg/g) | % catechin sorbed by soybean flour |
|---|---|---|
| 10 | 14 | 33 |
| 30 | 7 | 48 |
| 50 | 5 | 61 |
| 100 | 3 | 79 |

The amount of caffeine in the untreated and soybean flour-treated tea samples (n=1) was also tested. Caffeine is an alkaloid in the form of a derivative xanthine compound that, as a purine-based compound, exhibits aromatic character. Caffeine is a psychoactive stimulant that provides health benefits beyond the familiar increase in alertness and energy associated with coffee and tea consumption. The untreated and flour-treated tea samples described above were diluted 10 times in 0.1% acetic acid (1 µL glacial acetic acid and 1 mL water). Samples were subject to HPLC-MS and caffeine was quantified against a caffeine standard curve. The results are set forth in Table 13 below. The concentration of caffeine in soybean flour was determined to be approximately 2.9 mg/g.

TABLE 13

|  | Caffeine Concentration (mg/L) | Concentration of caffeine sorbed to defatted soy flour (mg/g) | % caffeine sorbed to SFDF |
|---|---|---|---|
| Tea sample | 471.3 | | |
| Tea + SFDF (30 g/L) | 383.1 | 2.9 | 19 |

The data show that yet another health-promoting polyphenol is efficiently and quantitatively sorbed (e.g., adsorbed) to plant flour, providing a quick, easy and inexpensive approach to concentrating natural products in an edible form.

Example 12. Sorption of 6-Gingerol to Soybean Flour

6-Gingerol (Sigma) was diluted in water to a concentration of 9 µg/ml. Full-fat soybean flour was added to the solution at a concentration of 30 g/L in a volume of 10 ml, mixed for 5 minutes and then centrifuged for 10 minutes at 4000 rpm. The supernatant was removed. Full-fat soybean flour was used as a control. Both the 6-gingerol solution before soybean flour treatment (i.e., plant juice) and that obtained after soybean flour treatment (i.e., plant liquor) were subjected to HPLC-MS; the injection volume for each sample was 10 µl. Results indicated that the soybean flour sorbed 63% of the 6-gingerol from the sample, as determined by calculating the percent decrease in peak area of 6-gingerol compared to the starting solution.

The data show that yet another phytochemical was efficiently and quantitatively sorbed (e.g., adsorbed) to plant flour, providing a quick, easy and inexpensive approach to concentrating natural products in an edible form.

Example 13. Sorption of Sesquiterpene Lactones from Chicory Root Extract

Dried chicory root was ground to a powder and 25 g was extracted in 500 ml of water for three hours in a 50° C. water bath with sonication. The water extract was separated from the plant material by filtration. Defatted soybean flour was mixed for 5 minutes with 50 ml of the chicory root extract at a concentration of 100 g/L followed by centrifugation (10 minutes, 15,000 rpm) and filtration of the supernatant. Untreated and soybean flour-treated chicory root extract were subjected to HPLC-MS; the injection volume for each sample was 10 µl. The amounts of the dihydrolactucin, lactucopicrin and dihydrolactucopicrin compounds present in the chicory root extract sorbed to the soybean flour were determined by calculating the percent decrease in peak area before and after treatment of the chicory extract with soybean flour. Results indicated that the soybean flour sorbed 40% of dihydrolactucin, 100% of lactucopicrin and 80% of dihydrolactucopicrin from the chicory root extract.

The data show that other phytochemicals were efficiently and quantitatively sorbed (e.g., adsorbed) to ground edible material in the form of plant flour, providing a quick, easy and inexpensive approach to concentrating beneficial natural products in an edible form.

Example 14. Compounds Bound and Subsequently Eluted from the Enriched Substance

An enriched substance was prepared by mixing defatted soybean flour and blueberry juice. The polyphenol/anthocyanin-enriched soybean flour (i.e., enriched substance) was separated from the juice by centrifugation and then freeze-dried. Defatted soybean flour (control) was mixed with water acidified with citric acid (pH 3.3) and then subjected to the same procedures. Acidic methanol (methanol:water:acetic acid; 70:20:5) was used to elute compounds from 2 g of the enriched substance and 2 g of the soybean flour control. Each round of elution consisted of adding 20 ml of acidic methanol to 2 g of powder followed by brief vortexing, sonication for 10 minutes and then centrifugation to remove the eluate. This process was repeated about 15 times. The eluates were vacuum evaporated to reduce the volume and then vacuum freeze-dried. The dried materials were resuspended in water (20 mg/ml), centrifuged, and then subjected to HPLC-MS analysis (10 µl samples). Compounds identified as being eluted from the enriched substance and soybean flour control are identified below in Table 14.

TABLE 14

| Compound | Mass (−/+ionization) | Soybean flour eluate (Control) | Enriched substance eluate |
|---|---|---|---|
| Diadzin | 415/417 | + | + |
| Genistein | 431/433 | + | + |
| Acetyl-diadzin or Soyasapogenol | 457/459 | + | + |
| Acetyl-genistin | 473/475 | + | + |
| Malonyl-diadzin | 501/503 | + | + |
| Malonyl-genistin | 517/519 | + | + |
| Malonyl-glycitin | 531/533 | + | + |
| Soyasaponin III | 795/797 | + | + |
| Chlorogenates | 353/355 | − | + |
| Grucopyranolsyloxy-pentan-2-yl-p-coumarate | 411/413 | − | + |
| Delphinidin-3-arabinosode | 433/435 | − | + |
| Quercitin-arabinoside [M + H] | 433/435 | − | + |
| Cyanidin-3-galactoside | 447/449 | − | + |
| Quercitin-3-rhamnoside | 447/449 | − | + |
| Malvidin-3-arabinoside | 461/463 | − | + |
| Delphinidin-3-galactoside | 463/465 | − | + |
| Quercetin-3-galactoside | 463/465 | − | + |
| Petunidin-3-galactoside | 477/479 | − | + |
| 3-MeO-quercetin-3-galactoside | 477/479 | − | + |
| Malvidin-3-galactoside | 491/493 | − | + |

This Example demonstrates that the sorbed natural products can be successfully eluted from the enriched substance for use in applications where it is desirable to provide the sorbed natural products free of the enriched substance/ground edible material matrix.

Example 15. Carotenoids from Carrot Juice were Found in Plant Liquor

Soybean flour (30 g/L) was added to 50 ml of carrot juice and mixed at room temperature for five minutes on a magnetic stir plate. The juice was separated from the soybean flour by centrifugation at 15,000 rpm (Beckman, JA-17 rotor) and the supernatant was decanted. Carotenoids, which are tetraterpenoids of two types, i.e., the xanthophylls and carotenes, were found in the plant liquor. Carotenoid structure is typically in the form of a polyene chain, occasionally with terminal rings. With or without rings, however, carotenoids do not have a dominant aromatic character, consistent with the poor adsorption results described below. By visual inspection it was obvious that the orange-colored carotenoid pigments were not sorbed (e.g., adsorbed) by the soy flour, but rather remained in solution in the plant liquor. The Example demonstrates that compounds other than soluble carbohydrates, fats and oils can be found in plant liquor. More particularly, the Example demonstrates that tetraterpenoids can be separated from at least a bioactive natural product using a method according to the present disclosure, with the tetraterpenoids found in a plant liquor.

Example 16. Blueberry Sweetener/Flavoring or Coloring

Soybean flour at 100 g/L was added to 2 L of blueberry juice and mixed at room temperature for thirty minutes. The mixture was then centrifuged for 30 minutes at 15,000 rpm (Beckman, JA-17 rotor) and the decanted supernatant (i.e., plant liquor) was subsequently filtered through Miracloth (Calbiochem) to further remove any particulate material. The supernatant was then concentrated through vacuum evaporation. The resulting substance was a pleasant-tasting blueberry syrup containing high levels of fructose, glucose, and sucrose, which are natural sugars in blueberries.

This Example demonstrates that the methods described herein are useful for the preparation of plant liquors comprising non-sorbable natural products (such as fructose, glucose, and sucrose), which can be further processed to produce natural sweeteners and flavoring. It is further contemplated that plant liquor will provide an economical source for other compounds, such as fats and oils, in a concentrated or unconcentrated form.

Example 17. Components of Enriched Substance and Plant Liquor Prepared from Blueberry Juice The following experiment was performed to identify the components of plant liquor and enriched substance.

Soybean flour at 100 g/L was added to 2 L of blueberry juice and mixed at room temperature for five minutes. The mixture was then centrifuged for 30 minutes at 15,000 rpm (Beckman, JA-17 rotor) and the enriched substance was separated from the decanted supernatant (i.e., plant liquor) as described in Example 16. The enriched substance was freeze-dried to obtain a powder and the supernatant was concentrated 3-fold by vacuum evaporation. Defatted soybean flour and blueberry juice from concentrate were used as controls. The enriched substance, plant liquor and control samples were subjected to various AOAC analyses to quantify the amount of calories, carbohydrates (sugars, in particular), moisture, ash, protein, fat and dietary fiber present in the samples. For example, the amount of protein in the samples was quantified by the Dumas method (reference AOAC Official Methods of Analysis (OMA), $18^{th}$ Ed., Official Method No. 992.15) using 6.25 as a nitrogen conversion factor; sugars were quantified by HPLC (AOAC OMA, $18^{th}$ Ed., Official Method No. 977.20 with modifications), dietary fiber was measured using AOAC (OMA), $18^{th}$ Ed., Official Method No. 991.43 with modification; fat was quantified by a gravimetric method (AOAC (OMA), $18^{th}$ Ed., Official Method Nos. 948.15, 922.06, 925.32, 950.50, 922.09 with modification); moisture was determined by vacuum oven (AOAC (OMA), $18^{th}$ Ed., Official Method Nos. 934.06, 969.38, 977.21 with modification) and ash was quantified by AOAC (OMA), $18^{th}$ Ed., Official Method No. 923.03. Carbohydrates are determined by the following calculation: Carbohydrates=100−(Moisture)−(Ash)−(Total Fat)−(Protein). Calories are determined by the following calculation: Calories=(4×Carbohydrates)+(9×Total Fat)+(4×Protein); Calories from fat=9×total fat.

The identified components of the various samples are provided below in Table 15.

TABLE 15

|  | Enriched substance | Soybean flour (Control) | Plant liquor | Blueberry juice (Control) |
|---|---|---|---|---|
| Carbohydrates | 51.6 | 35.8% | 71.6% | 61.2% |
| Calories (per 100 g) | 372 | 378 | 293 | 252 |
| Calories from fat (per 100 g) | 18 | 29 | 3 | 7 |
| Moisture | 6.929% | 3.234% | 25.204% | 36.943% |
| Ash | 2.539% | 6.420% | 1.979% | 1.104% |
| Protein | 37% | 51.3% | 0.890% | <0.625% |
| Total fat | 1.96% | 3.24% | 0.34% | 0.79% |
| Total dietary fiber | 18.4% | 18.3% | 1.5% | 1.7% |
| Raffinose | 0.106% | 0.980% | 0.244% | <0.1% |
| Stachyose | 0.450% | 5.28% | 1.29% | <0.1% |
| Fructose | 11.9% | 0.639% | 24.9% | 22.4% |
| Glucose | 10.4% | 0.102% | 24.0% | 21.4% |
| Sucrose | 0.826% | 8.51% | 2.47% | <0.1% |
| Maltose | <0.1% | <0.1% | <0.1% | <0.1% |
| Lactose | <0.1% | <0.1% | <0.1% | <0.1% |
| Total sugars | 23.1% | 9.25% | 51.4% | 43.8% |

Table 15 indicates that the concentration of sugars (glucose and fructose) in the enriched substance is higher than in the starting soybean flour. This apparent result is an artefact of the method used to produce the enriched substance described in this Example. The enriched substance was separated from the plant juice by allowing the enriched substance to settle solely under the force of gravity. This resulted in the formation of a wet enriched substance, which retained a significant amount of residual plant juice. When dried, this enriched substance had sugars from the juice dried with the matrix. Squeezing the juice out before or during or separation of enriched substance and plant liquor, using a different type of separation method (e.g., membrane- or drum-type centrifugation, vacuum filtration) would have removed most of the juice from the matrix leaving less sugar behind in the enriched substance fraction. As established in other Examples herein, however, the soluble carbohydrate content of the enriched substance was artefactly elevated due to incomplete separation of enriched substance and plant liquor. Enriched substance obtained without residual plant liquor, as disclosed in, for example, Example 6 contains minor amounts of the soluble carbohydrates.

The data demonstrate that the plant liquor comprises high percentages of fructose and glucose which can be used directly or further separated from the plant liquor and used as a natural sweetener.

Example 18. Isolation of Soluble Potato Proteins by Cranberry Juice Concentrate The following Example demonstrates that phenolic compounds present in cranberry juice concentrate are capable of sorbing (or forming complexes with) soluble proteins found in potato juice.

Total soluble potato proteins were extracted from fresh potato tubers (cv Russet Burbank) purchased in the local supermarket. Washed tubers (1 kg) were ground in the presence of 1 L of extraction solution containing 50 g/L sodium chloride and 50 ml/L acetic acid (pH 4.0). The resulting suspension was filtered by centrifugation (5 min at 5,000 g), and the clear supernatant containing total soluble potato proteins (i.e., potato juice) was used in the next step. Appropriate volumes of cranberry juice concentrate were added to 30 ml of potato juice to yield final concentrations of 0, 1, 3 and 10% cranberry juice concentrate, v:v, mixed and incubated overnight at 4° C. Precipitation of potato protein/cranberry phenolics complex was observed visually. Precipitated complexes had a reddish color due to the presence of anthocyanins (a family of colored phenolic compounds present in cranberry juice). The potato protein/cranberry phenolic complex was isolated by centrifugation (5 min at 5,000 g) and lyophilized overnight, resulting in dry, reddish to pink colored powder.

The concentration of total monomeric anthocyanins in untreated potato juice and cranberry juice concentrate-treated potato protein/cranberry phenolics complex (i.e., the dry, reddish to pink colored powder) was determined after elution with acidified methanol using the AOAC pH differential method adapted for a 96-well plate format and results were expressed as cyanidin-3-glucoside equivalents. Total soluble protein of the potato protein/cranberry phenolics complex was determined by BCA protein assay (Pierce). Protease inhibitory activity of the potato protein/cranberry phenolics complex was measured by Azocasein protease assay (Tomarelli et al J Lab Clin Med 1949 34(3):428-433) using trypsin as a model protease. The results of these assays are provided below in Table 16.

TABLE 16

| Sample | pH | Protein yield, (mg/g) | Eluted anthocyanin (mg/g complex) | PI Activity (TIU/mg protein complex) |
|---|---|---|---|---|
| Potato juice | 4.0 | — | — | — |
| +1% cranberry concentrate | 3.9 | 1.28 | 4.04 | 14 |
| +3% cranberry concentrate | 3.8 | 1.88 | 5.62 | 40 |
| +10% cranberry concentrate | 3.4 | 3.96 | 6.52 | 65 |

Results indicated that about 1 g of potato protein was pound to about 6.5 mg anthocyanin at the highest concentration used. One noteworthy class of protein cound in soluble potato protein is potato protease inhibitors. Potato protease inhibitors bound to the potato protein/cranberry phenolics complex retained their enzymatic activity as assed using the Azocasein protease assay, which was highest when 10% cranberry concentrate was used.

The data in this Example demonstrate that phenolic compounds are capable of sorbing (or forming complexes with) soluble proteins from plant juice, thus allowing for the isolation and use of such proteins using the methods described herein.

Example 19. Isolation of Thermostable Potato Protease Inhibitors by Cranberry Juice Concentrate The following Example demonstrates that phenolic compounds present in cranberry juice concentrate are capable of sorbing (or forming complexes with) potato protease inhibitors found in potato juice.

Total soluble potato proteins were extracted from fresh potato tubers (cv Russet Burbank) as described in Example 18. The clear supernatant was heated to 70° C. for 30 minutes and then cooled to 25° C. to precipitate the majority of the soluble potato proteins, with the exception of thermostable potato protease inhibitors (PPI). Precipitated proteins proteins were removed by centrifugation (5 min at 5,000 g), and the clear supernatant containing thermostable potato protease inhibitors was used in the next step.

Appropriate volumes of cranberry juice concentrate were added to 30 ml of potato protease inhibitor solution to yield final concentrations of 0, 1, 3 and 10% cranberry juice concentrate, v:v, and mixed overnight at 4° C. Precipitation of potato protease inhibitors/cranberry phenolics complex was observed. The potato protease inhibitors/cranberry phenolics complex was isolated by centrifugation (5 min at 5,000 g) and lyophilized overnight, resulting in a dry, red to pink colored powder. The concentration of total monomeric anthocyanins in untreated potato protease inhibitor solution and concentrate-treated potato protein inhibitor/cranberry phenolics complex (i.e., the dry, red to pink colored powder) was determined after elution with acidified methanol using the AOAC pH differential method adapted for a 96-well plate format and the results were expressed as cyanidin-3-glucoside equivalents.

Total soluble protein of the potato protein inhibitor/cranberry phenolics complex was determined by BCA protein assay (Pierce). Protease inhibitory activity of the potato protein/cranberry phenolics complex was measured by Azocasein protease assay (Tomarelli et al J Lab Clin Med 1949 34(3):428-433) using trypsin as a model protease. Results indicated that about 1 g of potato protease inhibitors were bound to about 1.6 mg anthocyanin at the highest concentration used. See Table 17 below.

TABLE 17

| Sample | pH | PPI yield, (mg/g) | Eluted anthocyanin (mg/g complex) | PI Activity (trypsin inhibitor units/mg protein complex) |
|---|---|---|---|---|
| Potato juice (PPI) | 4.0 | — | — | — |
| +1% cranberry concentrate | 3.9 | 0.48 | 0.21 | 61 |
| +3% cranberry concentrate | 3.8 | 1.16 | 1.02 | 76 |
| +10% cranberry concentrate | 3.5 | 2.28 | 1.63 | 84 |

Potato protease inhibitors bound to the potato protease inhibitors/cranberry phenolics complex retained their enzymatic activity, which was highest when 10% cranberry juice concentrate was used.

The data in this Example demonstrate that phenolic compounds are capable of sorbing (or forming complexes with) potato protease inhibitors, thus allowing for the isolation and use of such protease inhibitors using the methods described herein. More generally, the Example establishes that the methods described herein are suitable for obtaining any plant protein in the form of a sorbed complex, and that the methods of the disclosure are compatible with conventional protein purification techniques (heat in the case of the exemplified protease inhibitors).

Example 20. Isolation of Pineapple Proteases by Cranberry Juice Concentrate

The following Example demonstrates that phenolic compounds present in cranberry juice concentrate are capable of sorbing or forming complexes with proteins found in pineapple juice.

Total soluble pineapple proteins were extracted from fresh pineapple fruit purchased in the local supermarket. 1 kg of washed fruits was ground in the presence of 1 L of extraction solution containing 50 g/L sodium chloride. The resulting suspension was filtered by centrifugation (5 min at 5,000 g), and the clear supernatant containing total soluble pineapple proteins (pineapple juice) was used in the next step.

Appropriate volumes of cranberry juice concentrate were added to 30 ml of pineapple juice to yield final concentrations of 0, 1, 3 and 10% cranberry juice concentrate, v:v, and mixed overnight at 4° C. Precipitation of pineapple proteins/cranberry anthocyanin complex was observed. The pineapple proteins/cranberry anthocyanin complex was isolated by centrifugation (5 min at 5,000 g) and lyophilized overnight, resulting in dry, red to pink colored powder. The concentration of total monomeric anthocyanins in the untreated pineapple juice and concentrate-treated pineapple protein/cranberry phenolics complex (i.e., the dry, red to pink colored powder) was determined using the AOAC pH differential method after elution with acidified methanol adapted for a 96-well plate format and results were expressed as cyanidin-3-glucoside equivalents. It is likely that other cranberry phenolic compounds were also associated with the precipitated protein, and the method is not limited to the use of anthocyanidins.

Total soluble protein of the pineapple protein/cranberry phenolics complex was determined by BCA protein assay (Pierce). Protease activity of the pineapple protein/cranberry phenolics complex was measured by Azocasein protease assay using trypsin as a standard. Results indicated that approximately 3.7 mg anthocyanin was bound to 1 g of pineapple proteins at the highest concentration used, as shown in Table 18 below.

TABLE 18

| Sample | pH | Pineapple protein yield, (mg/g) | Eluted anthocyanin (mg/g complex) | PI Activity (Trypsin units/ mg protein complex) |
| --- | --- | --- | --- | --- |
| Pineapple juice | 3.5 | — | — | — |
| +1% cranberry concentrate | 3.4 | 0.36 | 0.363 | 35 |
| +3% cranberry concentrate | 3.1 | 1.20 | 0.52 | 80 |
| +10% cranberry concentrate | 2.9 | 4.68 | 3.71 | 91 |

Pineapple proteins bound to the pineapple proteins/cranberry phenolics complex retained their enzymatic activity, which was highest when 10% cranberry juice concentrate was used.

The data presented in this Example demonstrate that phenolic compounds are capable of sorbing (or forming complexes with) soluble proteins from pineapple juice, thus allowing for their isolation and use by the methods described herein. The Example demonstrates successful use of the methods of the disclosure to produce a sorbed form of another plant protein (pineapple protease v. potato protease inhibitor) from another plant juice (pineapple v. potato).

Example 21. Isolation and Purification of Papaya Proteases by Cranberry Juice Concentrate The following Example demonstrates that phenolic compounds present in cranberry juice concentrate are capable of sorbing (or forming complexes with) soluble proteins found in papaya juice.

Total soluble papaya proteins were extracted from fresh papaya fruit purchased in the local supermarket. 1 kg of washed papaya was ground in the presence of 1 L of extraction solution containing 50 g/L sodium chloride. The resulting suspension was filtered by centrifugation (5 min at 5,000 g), and the clear supernatant containing total soluble papaya proteins (papaya juice) was used in the next step.

Appropriate volumes of cranberry juice concentrate were added to 30 ml of papaya juice to yield final concentrations of 0, 1, 3 and 10% cranberry juice concentrate, v:v, and mixed overnight at 4° C. Precipitation of papaya proteins/cranberry phenolics complex was observed. The papaya proteins/cranberry phenolics complex was isolated by centrifugation (5 min at 5,000 g) and lyophilized overnight, resulting in dry, red to pink colored powder.

The concentration of total monomeric anthocyanins in untreated papaya juice and concentrate-treated papaya protein/cranberry phenolics complex (i.e., the dry, red to pink colored powder) was determined after elution with acidified methanol, using the AOAC pH differential method adapted for a 96-well plate format and the results were expressed as cyanidin-3-glucoside equivalents. It is likely and expected that other cranberry phenolic compounds were also associated with the precipitated protein.

Total soluble protein of the papaya protein/cranberry phenolics complex was determined by BCA protein assay (Pierce). Protease activity of the papaya protein/cranberry phenolics complex was measured by Azocasein protease assay using trypsin as a model protease. Results indicated that approximately 2.6 mg anthocyanin was bound to 1 g of papaya proteins at the highest concentration used, as shown in Table 19 below.

TABLE 19

| Sample | pH | Papaya protein yield, (mg/g) | Eluted anthocyanin (mg/g complex) | PI Activity (Trypsin units/ mg protein complex) |
| --- | --- | --- | --- | --- |
| Papaya juice | 4.6 | — | — | — |
| +1% cranberry concentrate | 3.9 | 1.68 | 0.22 | 51 |
| +3% cranberry concentrate | 3.5 | 3.64 | 0.78 | 95 |
| +10% cranberry concentrate | 2.9 | 5.48 | 2.55 | 111 |

Papaya proteins bound to the papaya proteins/cranberry phenolics complex retained their enzymatic activity, which was highest when 10% cranberry juice concentrate was used.

The data presented in this Example demonstrates that phenolic compounds are capable of sorbing (or forming complexes with) soluble proteins from papaya juice, thus allowing for their isolation and use in the methods described herein. The Example further establishes the breadth of plant juices, and plant proteins, amenable to the methods disclosed herein that yield sorbed complexes suitable for the variety of purposes described herein.

Example 22. Isolation of Milk Proteins

Skim milk (total fat 0 g per 240 ml, total protein 8 g per 240 ml) was purchased from Tuscan Dairy Farms in the local supermarket. Appropriate volumes of cranberry juice concentrate were added to 30 ml of milk to yield final concentrations of 0, 1, 3 and 10% cranberry juice concentrate, v:v, and mixed overnight at 4° C. Precipitation of milk proteins/cranberry phenolics complex was observed. The milk proteins/cranberry phenolics complex was isolated by centrifugation (5 min at 5,000 g) and lyophilized overnight, resulting in dry, red to pink colored powder. Use of regular 4% fat milk resulted in a formation of a similar precipitate, but with a more oily texture.

Milk protein binding and co-precipitation with anthocyanins was used as an indicator of the overall ability of cranberry phenolic compounds to bind and co-precipitate milk proteins. The concentration of total monomeric anthocyanins in untreated milk and concentrate-treated milk protein/cranberry phenolics complex (i.e., the dry, red to pink colored powder) was determined after elution with acidified methanol, using the AOAC pH differential method adapted for 96-well plate format. The results were expressed as cyanidin-3-glucoside equivalents. The difference in anthocyanin concentration between untreated and milk-treated concentrate samples was also used to estimate the concentration of anthocyanins bound to the milk proteins.

Total protein of the milk protein/cranberry anthocyanin complex was determined by BCA protein assay (Pierce). The results are provided in Table 20 below.

TABLE 20

| Sample | pH | Yield, (mg/ml milk) | Eluted anthocyanin (mg/g complex) | Sorbed anthocyanin (mg/g complex) | Sorbed anthocyanin to milk protein (%) |
|---|---|---|---|---|---|
| Skim milk | 6.8 | 0 | 0 | — | |
| +3% cranberry concentrate | 4.9 | 78.3 | 1.49 | 5.7 | 60.2 |
| +10% cranberry concentrate | 4.0 | 117.3 | 3.29 | 6.8 | 45.4 |
| +30% cranberry concentrate | 3.1 | 105.1 | 3.13 | 15.3 | 38.9 |

Results indicated that approximately 3.2 mg anthocyanin (as measured by eluting anthocyanins from the anthocyanin/milk protein complex with acidified methanol) or 15.3 mg anthocyanin (amount of anthocyanin bound to milk protein as determined by measuring the difference between untreated and milk-treated cranberry concentrate samples) was bound to 1 g of milk proteins at the highest concentration used. It was assumed that the concentration of the anthocyanins in the co-precipitate correlates with the concentrations of other cranberry phenolic compounds.

The data in this Example demonstrate that phenolic compounds present in cranberry juice are capable of sorbing (or forming complexes with) proteins present in milk, thus allowing for their isolation and use in methods described herein.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entireties.

From the foregoing it will be appreciated that, although specific embodiments of the invention have been described herein for purposes of illustration, various modifications may be made without deviating from the spirit and scope of the invention.

What is claimed is:

1. A method of producing an enriched substance in edible, solid form comprising a phytochemical from a plant juice consisting of:
   (a) combining the plant juice with an edible powder in powdered form to form an admixture containing an enriched solid substance comprising the phytochemical from the plant juice sorbed to the edible powder, wherein the edible powder is a plant flour or a protein powder; and
   (b) separating the solid enriched substance comprising the phytochemical from the plant juice sorbed to the edible powder from the admixture by centrifugation, filtration or sedimentation, thereby producing the enriched substance in edible, solid form.

2. The method of claim 1, wherein the plant juice comprises (a) material that has been homogenized, extracted, or pressed from a plant or plant part, or (b) a tea, an infusion, or a tincture from a plant or plant part.

3. The method of claim 2, wherein the plant part is selected from the group consisting of a bark, a flower, a berry, a fruit, a seed, a root, a nut, a leaf, and a stem.

4. The method of claim 1, wherein the plant flour is selected from the group consisting of soybean flour, defatted soybean flour, soy protein isolate, wheat flour, almond flour, amaranth flour, brown rice flour, buckwheat flour, cassava flour, chestnut flour, Chickpea flour, chuno flour, corn flour, cornstarch, glutinous rice flour, noodle flour, hazelnut flour, walnut flour, pea flour, bean flour, peanut flour, potato starch flour, rice flour, rye flour, tapioca flour, teff flour, arrowroot flour, taro flour, quinoa flour, mulga flour, ironweed flour, umbrella bush flour, tjuntjula flour, wakalpulka flour, witchetty bush flour, wiry wattle flour, Mitchell grass flour, nardoo flour, coconut flour, old man saltbush flour, and wangunu flour.

5. The method of claim 1, wherein the phytochemical is a proanthocyanidin, a flavan-3-ol, a hydrolyzable tannin, a phlorotannin, a gingerol, a sesquiterpene lactone, a sulforaphane, an isothiocyanate, an anthocyanin, resveratrol, quercetin, or caffeine.

6. The method of claim 1, wherein the comestible fluid is milk.

7. The method of claim 6, wherein the sorbable natural product is a milk protein.

8. The method of claim 5, wherein the phytochemical is an anthocyanin.

9. The method of claim 1, wherein the protein powder is selected from the group consisting of soy protein concentrate, soy protein isolate, wheat bran, oat bran, barley bran, rice bran, milk powder, egg powder, whey protein, gluten, and yeast powder.

* * * * *